(12) United States Patent
Ikoma et al.

(10) Patent No.: US 10,800,708 B2
(45) Date of Patent: Oct. 13, 2020

(54) SILVER-CONTAINING CALCIUM PHOSPHATE SINTERED BODY AND METHOD FOR PRODUCING SAME

(71) Applicants: Tokyo Institute of Technology, Tokyo (JP); KYOCERA Corporation, Kyoto-shi, Kyoto (JP)

(72) Inventors: Toshiyuki Ikoma, Tokyo (JP); Tomoaki Sugiyama, Tokyo (JP); Hiroaki Igashira, Tokyo (JP); Yugo Fukuyama, Tokyo (JP); Michimasa Kamo, Kyoto (JP); Masayuki Kyomoto, Kyoto (JP); Takashi Sasaki, Kyoto (JP)

(73) Assignees: TOKYO INSTITUTE OF TECHNOLOGY, Tokyo (JP); KYOCERA CORPORATION, Kyoto-Shi, Kyoto (JP)

( * ) Notice: Subject to any disclaimer, the term of this patent is extended or adjusted under 35 U.S.C. 154(b) by 63 days.

(21) Appl. No.: 16/080,407

(22) PCT Filed: Feb. 28, 2017

(86) PCT No.: PCT/JP2017/007818
§ 371 (c)(1),
(2) Date: Feb. 21, 2019

(87) PCT Pub. No.: WO2017/150539
PCT Pub. Date: Sep. 8, 2017

(65) Prior Publication Data
US 2019/0177229 A1      Jun. 13, 2019

(30) Foreign Application Priority Data
Feb. 29, 2016   (JP) .................................. 2016-037207

(51) Int. Cl.
*C04B 35/447* (2006.01)
*A61L 27/56* (2006.01)
(Continued)

(52) U.S. Cl.
CPC ............ *C04B 35/447* (2013.01); *A61L 27/12* (2013.01); *A61L 27/425* (2013.01); *A61L 27/54* (2013.01);
(Continued)

(58) Field of Classification Search
CPC ... C04B 35/447; C04B 2235/85; A61L 27/54; A61L 27/425; A61L 2300/104;
(Continued)

(56) References Cited

U.S. PATENT DOCUMENTS 4,846,838 A * 7/1989 Takai ........................ A61F 2/28
424/422
2010/0150980 A1    6/2010 Bokorny et al.
(Continued)

FOREIGN PATENT DOCUMENTS

| JP | 2009-186443 A | 8/2009 |
| JP | 2010-523344 A | 7/2010 |
| JP | 2012-513971 | 6/2012 |

OTHER PUBLICATIONS

Akhavan et al. Synthesis of antimicrobial silver/hydroxyapatite nanocompositeby gamma irradiation. Radiation Physics and Chemistry vol. 98, May 2014, pp. 46-50.*
(Continued)

*Primary Examiner* — Noah S Wiese
(74) *Attorney, Agent, or Firm* — Volpe and Koenig, P.C.

(57) ABSTRACT

The object of the present invention is to provide an antibacterial material capable of sustaining antibacterial properties for a long time. The object can be solved by a silver-containing calcium phosphate sintered body having
(Continued)

silver particles therein, wherein an average particle diameter of the silver particles is 0.01 to 0.5 µm.

26 Claims, 14 Drawing Sheets

(51) Int. Cl.
| | | |
|---|---|---|
| *A61L 27/42* | (2006.01) | |
| *C01B 25/32* | (2006.01) | |
| *A61L 27/54* | (2006.01) | |
| *A61L 27/12* | (2006.01) | |
| *G01N 21/65* | (2006.01) | |

(52) U.S. Cl.
CPC .............. *A61L 27/56* (2013.01); *C01B 25/32* (2013.01); *G01N 21/658* (2013.01); *A61L 2300/104* (2013.01); *A61L 2300/404* (2013.01); *A61L 2400/12* (2013.01); *A61L 2430/02* (2013.01); *A61L 2430/12* (2013.01); *C04B 2235/408* (2013.01); *C04B 2235/443* (2013.01); *C04B 2235/5427* (2013.01); *C04B 2235/5436* (2013.01); *C04B 2235/652* (2013.01); *C04B 2235/666* (2013.01); *C04B 2235/85* (2013.01)

(58) Field of Classification Search
CPC ........... A61L 2300/404; A61L 2430/02; A61L 2400/12; C01B 25/32
See application file for complete search history.

(56) References Cited

U.S. PATENT DOCUMENTS

| | | |
|---|---|---|
| 2012/0040005 A1 | 2/2012 | Moya Corral et al. |
| 2014/0142717 A1 | 5/2014 | Tanaka et al. |

OTHER PUBLICATIONS

Hashimoto, K, et al., "Preparation of Hydroxyapatite Fine Powder with Noble Metal Particles by Spray Pyrolysis Method," Inorganic Materials, vol. 6, Nov. 1999, pp. 463-467.

Akhavan, A., et al., "Synthesis of antimicrobial silver/hydroxyapatite nanocomposite by gamma irradiation," Radiation Physics and Chemistry, vol. 98, (2014) pp. 46-50.

Rajendran, A., et al., "Synthesis, phase stability of hydroxyapatite-silver composite with antimicrobial activity and cytocompatability," Ceramics International (Netherlands), vol. 40 (2014) pp. 10831-10838.

Paraskevas, S., et al., "A systematic review and meta-analyses on C-reactive protein in relation to periodontitis," Journal of Clinical Periodontology (Netherlands) 2008, vol. 35, pp. 277-291.

Extended European Search Report dated Oct. 14, 2019 for the European Patent Application No. 17760005.3.

Parakhonskiy et al., "Size controlled hydroxyapatite and calcium carbonate particles: Synthesis and their application as templates for SERS platform," Colloids and Surfaces B: Biointerfaces, vol. 118, pp. 243-248 (2014).

Jennings et al., "Bacterial inhibition by chitosan coatings loaded with silver-decorated calcium phosphate microspheres," Thin Solid Films, vol. 596, pp. 83-86 (2015).

Bukreeva et al., "Formation of silver nanoparticles on shells of polyelectrolyte capsules using silver-mirror reaction," Colloid Journal, 71: 596 (2009).

Saravanan et al., "Preparation, characterization and antimicrobial activity of a bio-composite scaffold containing chitosan/nano-hydroxyapatite/nano-silver for bone tissue engineering," International journal of biological macromolecules 49(2):188-93 (2011).

Ciobanu et al., "Hydroxyapatite-silver nanoparticles coatings on porous polyurethane scaffold," Materials Science and Engineering: C, vol. 35, pp. 36-42 (2014).

\* cited by examiner (a)

(b)

Example of measured area

SILVER-CONTAINING CALCIUM PHOSPHATE SINTERED BODY AND METHOD FOR PRODUCING SAME

TECHNICAL FIELD

The present invention relates to a silver-containing calcium phosphate sintered body and a method for preparing the same. According to the present invention, a biomaterial capable of maintaining an antibacterial activity can be provided.

BACKGROUND ART

Antibacterial materials having antibacterial activity have been currently used in various fields such as medical applications, living goods, photocatalysts, air conditioning materials, etc. As an antibacterial component of the antibacterial materials, metal ions are frequently used. With regard to the antibacterial activity of metal ions, silver ion and mercury ion are particularly active, and zinc ion, copper ion, and cadmium ion are followed by high activity. Silver ion is characterized by its high safety, high antibacterial activity against bacteria, wide antibacterial spectrum, and usability even at high temperature, and therefore is just used as antimicrobial components of antibacterial materials.

On the other hand, for some antimicrobial materials in the medical field, it is necessary to sustain long-term antimicrobial action. For example, a peri-implant mucositis may develop in implant treatment. Peri-implant mucositis is an inflammation that is developed in the implant and its surrounding mucosa, and is caused by retention of dental plaque around the implant and a proliferation of periodontopathic bacteria. When the peri-implant mucositis progresses, inflammation reaches bones of the jaw supporting the implant. Then, if left unattended, it progresses to a peri-implantitis where the implant falls off. The peri-implantitis is known to develop in about 20% of patients in 5 to 10 years after implant treatment, which is a major problem (Non-Patent literature 2). In addition, in surgical treatment of orthopedic surgery using indwelling implants, late infectious diseases occurring from 3 months to 10 years or more after surgery are a problem Additionally, in surgical treatment and orthopedic surgery using indwelling type implants, late-onset infections occurring from 3 months to 10 years or more after surgery are a problem. The infection of the implant body which is one of the causes of late-onset infection, occurs in the deep within the body, and thus it often displays serious symptoms. Therefore an establishment of an effective solution is expected.

CITATION LIST

Non-Patent Literature

[Non-patent literature 1] Ceramics International (Netherlands) 2014, vol. 40, p. 10831-10838
[Non-patent literature 2] Journal of Clinical Periodontology (Netherlands) 2008, vol. 35, p. 286-291

SUMMARY OF INVENTION

Technical Problem

In order to prevent infection of the implant body, it is important to suppress growth of bacteria on a surface of the implant body and its surroundings. The present inventors considered to suppress the growth of bacteria by using an antibacterial material as the implant material. However, there are no antibacterial materials capable of sustaining antimicrobial properties for a long period of 5 to 10 years after surgery. For example, Non-Patent Literature 1 discloses a silver-supported material obtained by adding apatite particles to silver nitrate particles, and sintering the whole. The present inventors considered using the silver-supported material disclosed in the Non-Patent Literature 1 as the implant material. However, the silver-supported material was considered to be unable to sustain antibacterial properties over a long period, because silver particles are supported on the surface of apatite particles.

That is, the conventional silver supported material is one in which hydroxyapatite and silver particles are merely mixed, and thus the silver particles are dissolved immediately, and long-term antibacterial properties could not be maintained.

Accordingly, the object of the present invention is to provide an antibacterial material capable of sustaining antibacterial properties for a long time.

Solution to Problem

The present inventors have conducted intensive studies into the antibacterial material capable of sustaining antibacterial properties for a long time. As a result, the present inventors surprisingly found that a silver-containing calcium phosphate sintered body containing silver particles therein is obtained by applying aldehyde to calcium phosphate porous particles, and forming particles with silver reacting to aldehyde and calcining the same.

The present invention is based on the above findings.
Namely, the present invention relates to:
[1] a silver-containing calcium phosphate sintered body having silver particles therein, wherein an average particle diameter of the silver particles is 0.01 to 0.5 μm,
[2] the silver-containing calcium phosphate sintered body of the item [1], wherein the silver particles are present at a grain boundary of the calcium phosphate sintered body,
[3] the silver-containing calcium phosphate sintered body of the item [1] or [2], wherein the calcium phosphate sintered body is a calcium phosphate sintered particle, having an average particle diameter of 10 to 300 μm,
[4] the silver-containing calcium phosphate sintered body of the item [3], wherein 95% or more of the silver particles are contained within a radius of 80% from the center in a cross-section of the silver-containing calcium phosphate sintered particle,
[5] the silver-containing calcium phosphate sintered body of the item [1] or [2], wherein the silver-containing calcium phosphate sintered body is molded,
[6] the silver-containing calcium phosphate sintered body of any one of the items [1] to [5], wherein an amount of the silver particles is 0.03 to 40% by weight,
[7] the silver-containing calcium phosphate sintered body of any one of the items [1] to [6], wherein five or more the silver particles are contained per a cross-section of 100 μm² of the silver-containing calcium phosphate sintered body,
[8] the silver-containing calcium phosphate sintered body of any one of the items [1] to [7], wherein calcium phosphate is selected from the group consisting of hydroxyapatite, calcium dihydrogen phosphate, calcium dihydrogen phosphate hydrate, calcium monohydrogen phosphate, calcium monohydrogen phosphate hydrate, octacalcium phosphate, and tricalcium phosphate,

[9] the silver-containing calcium phosphate sintered body of any one of the items [1] to [8], wherein the silver-containing calcium phosphate sintered body has an antibacterial property,

[10] a method for preparing a silver-containing calcium phosphate sintered body, comprising steps of; (1) applying a reducing agent to calcium phosphate porous particles, (2) immersing the reducing agent-applied calcium phosphate porous particle in an aqueous solution containing silver complex to precipitate silver particles within the calcium phosphate porous particles, and (3) calcining the silver particle-precipitated calcium phosphate porous particle,

[11] the method for preparing a silver-containing calcium phosphate sintered body of the item [10], wherein the reducing agent is aldehyde,

[12] the method for preparing a silver-containing calcium phosphate sintered body of the item [10] or [11], wherein the application of the reducing agent is an aldehyde vapor deposition,

[13] the method for preparing a silver-containing calcium phosphate sintered body of any one of the items [10] to [12], wherein the aqueous solution containing silver complex is an ammoniacal silver nitrate aqueous solution,

[14] the method for preparing a silver-containing calcium phosphate sintered body of any one of the items [10] to [13], wherein the silver particle-precipitated calcium phosphate porous particles are molded and the resulting molded body is calcined in the calcining step (3),

[15] the method for preparing a silver-containing calcium phosphate sintered body of any one of the items [10] to [14], wherein the silver particle-precipitated calcium phosphate porous particles are calcined while pressure molding in the calcining step (3),

[16] the method for preparing a silver-containing calcium phosphate sintered body of the item [15], wherein the method of calcining and pressure-molding is a hot pressing method or a spark plasma sintering method,

[17] the method for preparing a silver-containing calcium phosphate sintered body according to any one of claims 10 to 16, wherein calcium phosphate is selected from the group consisting of hydroxyapatite, calcium dihydrogen phosphate, calcium dihydrogen phosphate hydrate, calcium monohydrogen phosphate, calcium monohydrogen phosphate hydrate, octacalcium phosphate, and tricalcium phosphate,

[18] an implant body comprising the silver-containing calcium phosphate sintered body of any one of the item [1] to [9],

[19] a silver-containing calcium compound porous particle containing silver particles, wherein an average particle diameter of the silver particle is 0.01 to 0.5 μm,

[20] the silver-containing calcium compound porous particle of the item [19], wherein an average particle diameter of the silver-containing calcium compound porous particle is 1.0 to 300 μm,

[21] the silver-containing calcium compound porous particle of the item according to claim 19 or 20, wherein an amount of the silver particles is 0.03 to 40% by weight

[22] the silver-containing calcium compound porous particle of any one of the items [19] to [21], wherein the calcium compound is selected from the group consisting of calcium phosphate, calcium carbonate, calcium sulfate, and calcium oxide,

[23] the silver-containing calcium compound porous particle of the item [22], wherein calcium phosphate is selected from the group consisting of hydroxyapatite, calcium dihydrogen phosphate, calcium dihydrogen phosphate hydrate, calcium monohydrogen phosphate, calcium monohydrogen phosphate hydrate, octacalcium phosphate, and tricalcium phosphate,

[24] a method for preparing a silver-containing calcium compound porous particle, comprising steps of: (1) applying a reducing agent to the calcium compound porous particle, and (2) immersing the reducing agent-applied calcium compound porous particle in an aqueous solution containing silver complex to precipitate silver particles on a surface of particle constituting the calcium compound porous particle,

[25] the method for preparing a silver-containing calcium compound porous particle of the item [24], wherein the reducing agent is aldehyde,

[26] the method for preparing a silver-containing calcium compound porous particle of the item [24] or [25], wherein the application of the reducing agent is an aldehyde vapor deposition,

[27] the method for preparing a silver-containing calcium compound porous particle of any one of the items [24] to [26], wherein the aqueous solution containing silver complex is an ammoniacal silver nitrate aqueous solution,

[28] a method of Raman spectroscopic analysis, comprising the steps of: (1) applying a substance to be tested to the silver-containing calcium compound porous particle of any one of the items [19] to [23], (2) irradiating the substance-applied, silver-containing calcium compound porous particle with laser light, and (3) detecting a Raman scattering light or

[29] the method of Raman spectroscopic analysis of the item [28], wherein the application in the step (1) is done by immersion of the silver-containing calcium compound porous particles into a liquid containing the substance to be tested, or a placement of the liquid containing the substance to be tested on the silver-containing calcium compound porous particles.

Advantageous Effects of Invention

According to the silver-containing calcium phosphate sintered body of the present invention, an antibacterial material capable of eluting silver, which is an antibacterial metal ion in the long term, can be provided. That is, the silver-containing calcium phosphate sintered body of the present invention can maintain antibacterial properties for a long period because the average particle diameter of silver particles contained therein is 0.01 to 0.5 μm. Particularly, a silver-containing calcium phosphate sintered body in which silver particles are encapsulated at grain boundaries of a sintered body can maintain antibacterial property for a long period. Therefore, it can be effectively used as an antibacterial material in fields requiring long-lasting antibacterial properties.

Further, the antibacterial material of the present invention contains silver particles therein, and therefore, when antibacterial material dissolves due to a low pH, silver is eluted and can exhibit antibacterial properties. Therefore, for example, when an inflammation occurs in a living body and the inflammation site acidifies, the antibacterial material dissolves and silver is released and then bacterial growth can be suppressed by its antibacterial activity. Therefore, for example, in the case that the silver-containing calcium phosphate sintered body of the present invention is used as a dental implant material, if the inflammation develops around the implant after implantation and the pH of the surrounding tissue decreases, the silver-containing calcium phosphate sintered body dissolves. Then, the silver therein is released, and thereby it is possible to prevent peri-implantitis.

Furthermore, the silver-containing calcium phosphate sintered body can be used as raw material for the implant body in addition to use by itself. For example, calcium phosphate particles may be fixed on the surface of the implant body for the purpose of improving bone affinity. By using the silver-containing calcium phosphate sintered body as raw material for the calcium phosphate particles, it is possible to obtain an implant body having an antibacterial property for a long period, as in the case where the silver-containing calcium phosphate sintered body is used alone.

Highly sensitive Raman spectroscopic analysis can be performed by using the silver-containing calcium compound porous particle of the present invention as a carrier for supporting a substance to be tested in Raman spectroscopic analysis. For high sensitivity, local surface Plasmon of noble metal nanoparticles, which is called "surface-enhanced Raman scattering", is used. When silver nanoparticles which are Plasmon active metals are arranged at a certain distance, an electric field in which local surface Plasmon induced by light irradiation are enhanced, i.e. a hot spot is generated. When the substance to be tested approaches the silver nanoparticles, Raman scattering peculiar to the substance to be tested generates. In particular, Raman scattering is enhanced by $1 \times 10^8$ times in the vicinity of the hot spot. This phenomenon is called "surface-enhanced Raman scattering (SERS)". Since Raman scattering is peculiar to substances, it is possible to identify and quantify a substance to be tested in a label-free manner.

Further, Raman spectroscopic analysis of a trace amount of the substance to be tested can be conducted because the matrix is a calcium compound having an excellent adsorption property and the substance to be tested is easily adsorbed on the surface thereof. In particular, in the silver-containing calcium compound porous body obtained by the present invention, silver particles having an average particle diameter of 0.01 to 0.5 μm are dispersed on the surface of the calcium compound. Thus, since a very low concentration of the substance to be tested can be adsorbed to, concentrated in, and collected in the calcium compound, highly sensitive Raman spectroscopic analysis can be performed.

Furthermore, in the present invention, a reducing agent is applied to the calcium compound to precipitate the silver nanoparticles. Thus, since the reducing agent is applied to limited sites, it is possible to precipitate the silver nanoparticles only at the limited sites. Therefore, the silver nanoparticles are localized at a specific position, and thus the SERS phenomenon can be dominantly observed.

DESCRIPTION OF EMBODIMENTS

[1] Silver-Containing Calcium Phosphate Sintered Body

Figure 1:
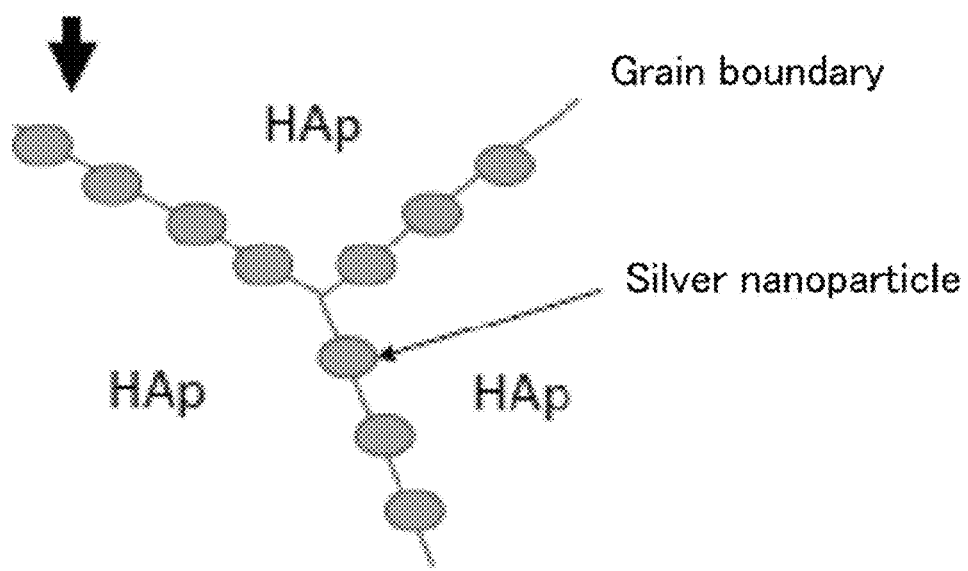
FIG. 1 is a view showing a localization of the silver particles in the silver-containing calcium phosphate sintered body of the present invention.

The silver-containing calcium phosphate sintered body of the present invention contains silver particles therein, and has an average particle diameter of 10 to 500 nm (0.01 to 0.5 μm). The silver particles are preferably present at a grain boundary. When the silver particles are present at the grain boundary, it is difficult to form large particles. Thus, the silver particles having an average particle diameter of 10 to 500 nm are often present at the grain boundary.

The form of the silver-containing calcium phosphate sintered body of the present invention may be a calcium phosphate sintered particle, and may be a calcium phosphate sintered compact wherein the calcium phosphate sintered particles are molded by a pressure molding method, a hot pressing method, a cold isostatic pressing method, an extrusion molding method, an injection pushing molding method and a hot isostatic pressing method. In the sintered compact, a shape thereof can be appropriately determined depending on the application. For example, a rectangular column, a pyramid, a cylinder, a cone, a donut or a spherical shape can be selected.

Further, the silver particles cannot be prevented from being present in the particles of the silver-containing calcium phosphate sintered body.

When the silver-containing calcium phosphate sintered body is the calcium phosphate sintered particle, the average particle diameter of the calcium phosphate sintered particle is not particularly limited. However, the upper limit of the average particle diameter is preferably 300 μm or less, more preferably 100 μm or less, even more preferably 40 μm or less. The lower limit of the average particle diameter is preferably 0.1 μm or more, more preferably 1 μm or more, even more preferably 2.5 μm or more, most preferably 4 μm or more. The average particle diameter can be measured by, for example, a laser diffraction apparatus for measuring particle size distribution using a laser diffraction scattering method, or a scanning electron microscope image.

Further, the diameter (particle size) of the calcium phosphate sintered particle is not particularly limited, but preferably 0.01 to 3000 μm, more preferably 0.5 to 300 μm, even more preferably 1 to 40 μm.

Furthermore, the silver-containing calcium phosphate sintered body of the present invention may be a silver-containing calcium phosphate sintered body consisting of calcium phosphate sintered particles containing silver particles, wherein 95% or more of the silver particles are contained within a radius of 80% from a center in a cross-section of the silver-containing calcium phosphate sintered particle.

<<Calcium Phosphate>>

As a calcium phosphate used for the calcium phosphate sintered body, there may be mentioned a group of compounds such as $Ca_3(PO_4)_2$, $Ca_3(PO_4)_2$, $Ca_{10}(PO_4)_6(OH)_2$, $Ca_4O(PO_4)_2$, $CaP_4O_{11}$, $Ca(PO_3)_2$, or $Ca_2P_2O_7$. In particular, hydroxyapatite, tetracalcium phosphate, or tricalcium phosphate is preferable, and hydroxyapatite is the most preferable. Hydroxyapatite is one of calcium phosphates which accounts for 60% to 80% of components of bone in a body, and a basic component thereof is a compound represented by the composition formula: $Ca_{10}(PO_4)_6(OH)_2$. A part of Ca contained in hydroxyapatite may be replaced with one or more elements selected from Sr, Ba, Mg, Fe, Al, Y, La, Na, K, H, or the like. Further, a part of ($PO_4$) may be replaced with one or more elements selected from $VO_4$, $BO_3$, $SO_4$, $CO_3$, $SiO_4$ or the like. Furthermore, a part of (OH) may be replaced with F, Cl, O, $CO_3$ or the like. In addition, a part of these elements may be lacking.

The calcium phosphate sintered body may be one obtained from hydroxyapatite and tricalcium phosphate, hydroxyapatite and tetracalcium phosphate, or tetracalcium phosphate and tricalcium phosphate.

<<Silver Particle>>

The silver particle contained in the silver-containing calcium phosphate sintered body of the present invention is not limited, but preferably a particle of silver element. For example, if the silver particle is prepared from $Ag_2O$ or $Ag_3PO_4$ having high solubility, the initial elution amount increases and it may be difficult to maintain antibacterial properties for a long period. The bacterium growth inhibitory activity of silver ion is highly safe, and it has strong antibacterial action against bacteria and broad antibacterial spectrum. For example, the minimum inhibitory concentration (MIC) for *Escherichia coli, Pseudomonas aeruginosa, Salmonella*, and *Klebsiella pneumoniae* is 0.78 mg/L, and the minimum inhibitory concentration (MIC) against *Staphylococcus aureus* is 6.3 mg/L. That is, the silver ion exhibits an excellent bacterial growth inhibitory activity.

As above, the silver particle contained in the silver-containing calcium phosphate sintered body of the present invention is the particle of silver element. However, it may contain silver compounds, and a part of sintered body other than silver particles may contain silver compounds. That is, the silver-containing calcium phosphate sintered body can contain silver compounds such as $Ag_2O$ or $Ag_3PO_4$ other than silver element. As mentioned above, $Ag_2O$ or $Ag_3PO_4$ exhibits high initial elution amounts, but that does not adversely affect the antibacterial property of silver element.

The average particle diameter of the silver particle is not limited as long as the effect of the present invention can be achieved. However, the upper limit of the average particle diameter is preferably 0.5 μm or less, more preferably 0.25 μm or less. The lower limit of the average particle diameter is preferably 0.01 μm or more, more preferably 0.05 μm or more, even preferably 0.1 μm or more. As the average particle diameter is in the above range, silver particles can be contained in the grain boundary of the calcium phosphate sintered body, and the antibacterial properties can be maintained for a long period.

The average particle diameter of the silver particle may be measured by, for example, the following method.

The cross-section of the silver-containing calcium phosphate sintered body is observed by a scanning electron microscope. At this time, a cross-section prepared by ion milling after implanting the sintered body in a resin may be observed, or a fracture cross-section of the sintered body may be observed. Via scanning electron microscope, silvers having different densities can be more clearly distinguished by photographing a backscattered electron image. The average particle diameter of silver can be semi-automatically measured by using electron microscopic images photographed at magnifications of ×3000 and ×10000, and an image processing/image analysis software. Alternatively, the average particle diameter can be measured manually from these electron microscopic images using measurement software.

(Amount of Silver Particles)

The amount of the silver particles in the calcium phosphate sintered body is not particularly limited. However, the lower limit of the amount of the silver particles is preferably 0.03% by weight or more, more preferably 0.1% by weight or more, more preferably 1% by weight or more, even more preferably 5% by weight or more, most preferably 7% by weight or more. The upper limit of the amount of the silver particles is also limited, but preferably 40% by weight or less, more preferably 30% by weight or less, more preferably 20% by weight or less, even more preferably 15% by weight or less, most preferably 11% by weight or less. As the amount of the silver particles is in the above range, the antibacterial properties can be maintained for a long period.

For example, the amount of the silver particles may be measured by the following method.

A predetermined amount of the silver-containing calcium phosphate sintered body is pulverized, and a predetermined amount of powder is fully dissolved in a 0.1 mol/L nitric acid aqueous solution. Then, the weight percentage of silver in silver-containing calcium phosphate sintered body can be determined by quantitating silver ions in the solution using inductively coupled plasma emission spectrometry (ICP).

(Area Ratio of Silver Particles)

The amount of the silver particles in the calcium phosphate sintered body can be represented in the cross-section area of the silver particles in the cross-section of the calcium phosphate sintered body. The ratio of the cross-section area of silver particles in the cross-section area of the calcium phosphate sintered body is not limited, but preferably 0.03% or more, more preferably 2% or more, even more preferably 3% or more. The upper limit of the ratio of the cross-section area of silver particles in the cross-section area of the calcium phosphate sintered body is, for example, 20% or less.

If the cross-section area in the calcium phosphate sintered body is too small, the ratio of the cross-section area of the silver particles may vary depending upon the sampling. Therefore, the cross-section area to be measured in the calcium phosphate sintered body is preferably 12.5 μm$^2$ or more, more preferably 100 μm$^2$ or more. More specifically, it is preferable to calculate the ratio of the cross-section area of the silver particles by measuring the total cross-section area of 100 μm$^2$ in the calcium phosphate sintered body. Further, in the case of the calcium phosphate sintered compact wherein the calcium phosphate sintered body is molded by pressurization or the like, the cross-section area of the silver particles can be calculated in an arbitrary cross-section of the calcium phosphate sintered body. On the other hand, in the case of the sintered particle of the calcium phosphate sintered body, if the cross-section of one particle is too small (for example, if the cross-section is an end of the particle), the ratio of the cross-section area of the silver particles may vary. Therefore, it is preferable to calculate the ratio of the cross-section area of the silver particles in the cross-section area of the sintered particle of 100 μm$^2$ by totaling the cross-section areas of the sintered particles having a cross-section area of 20 μm$^2$ or more.

(Number of Silver Particle)

The amount of the silver particles in the calcium phosphate sintered body can be represented by the number of the silver particles in the cross-section of the calcium phosphate sintered body. For example, the silver-containing calcium phosphate sintered body contains 5 or more silver particles of 0.05 to 0.5 μm per 100 μm² cross-section area of the silver-containing calcium phosphate sintered body. The lower limit of the number of the silver particles is preferably 10 or more, more preferably 20 or more, even more preferably 40 or more. The upper limit of the number of the silver particles is preferably 1000 or less, more preferably 500 or less.

(Distribution of Silver Particle)

When the calcium phosphate sintered body of the present invention is the calcium phosphate sintered particle, 95% or more of the silver particles (95% or more of cross-section area of the silver particles) are preferably contained within a radius of 80% from a center in a cross-section of the calcium phosphate sintered particle, but it is not limited thereto. That is to say, the calcium phosphate sintered particle containing the silver particles at the center of the calcium phosphate sintered particle and few silver particles near the surface, is preferable. An elution of silver particles from calcium phosphate sintered particle at an early stage can be prevented by containing the silver particles at the center of calcium phosphate sintered particle, and the antibacterial properties can be maintained for a long period.

If the cross-section of the calcium phosphate sintered particle is too small (if the cross-section is an end of the particle), it is difficult to accurately measure the amount of silver particles. Therefore, it is preferable to measure the distribution of silver particles in a particle having a diameter of 4 μm or more, that is, a cross-section area of 12.6 μm² or more.

(Grain Boundary)

Figure 20:
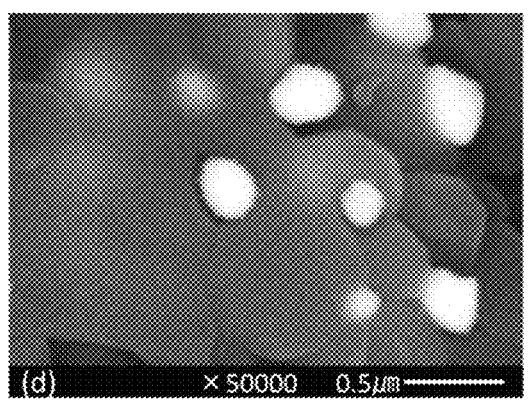
FIG. 20 is an image from a high magnification backscattered electron microscope of a fracture cross-section of the silver-containing calcium phosphate sintered compact obtained in Example 7.

In the silver-containing calcium phosphate sintered body of the present invention, a silver-containing calcium phosphate sintered body wherein the silver particles are present at a grain boundary of the calcium phosphate sintered body, is preferable, but it is not limited thereto. The grain boundary, which is formed by a growth of polycrystalline bodies during the high-temperature calcining process, means an interface between two or more polycrystalline bodies. The silver-containing calcium phosphate sintered body of the present invention can be obtained by, for example, the following method for preparing a silver-containing calcium phosphate sintered body. The silver element bonded to the reducing agent being present in pores of the calcium phosphate porous particle is calcined to fix the silver particles in the grain boundary of the calcium phosphate as shown in FIG. 1 and FIG. 20. An elution of silver particles from calcium phosphate sintered particle at an early stage can be prevented by fixing the silver particles in the grain boundary of calcium phosphate, and the antibacterial properties can be maintained for a long period.

(Silver Elution Amount)

A silver elution amount of the silver-containing calcium phosphate sintered body of the present invention is kept low, because the silver particles are fixed within calcium phosphate.

When 20 mg of silver-containing calcium phosphate sintered particles are applied to 10 mL of Dulbecco's phosphate buffer solution (D-PBS, pH 7.3) and inverse at 37° C., the silver elution amount after 6 hours or 12 hours is not limited, but preferably 800 ppb or less, more preferably 600 ppb or less, even more preferably 400 ppb or less, most preferably 200 ppb or less.

When 5 mg of silver-containing calcium phosphate sintered particles are applied to 10 mL of acetic acid-sodium acetate buffer solution (pH5.5, 0.8 mol/L) and inverse at 37° C., the silver elution amount after 24 hours, 48 hours, or 72 hours is not limited, but preferably 6 ppm or less, more preferably 4 ppm or less, even more preferably 1 ppm or less, most preferably 0.5 ppm or less.

[2] Method for Preparing a Silver-Containing Calcium Phosphate Sintered Body

A method for preparing a silver-containing calcium phosphate sintered body, comprises the steps of (1) applying a reducing agent to calcium phosphate porous particles, (2) immersing the reducing agent-applied calcium phosphate porous particle in an aqueous solution containing silver complex to precipitate silver particles within the calcium phosphate porous particles, and (3) calcining the silver particle-precipitated calcium phosphate porous particle (hereinafter, sometimes referred to as silver containing calcium phosphate porous particle).

(1) Step for Application of Reducing Agent

In the step for application of reducing agent (1), the reducing agent is applied to the calcium phosphate porous particles.

(Calcium Phosphate Porous Particles)

The calcium phosphate porous particles are obtained by preparing calcium phosphate crystals and forming particles. For example, the calcium phosphate crystals may be prepared using calcium phosphate such as, $Ca_3(PO_4)_2$, $Ca_{10}(PO_4)_6(OH)_2$, $Ca_4(PO_4)_2$, $CaP_4O_{11}$, or $Ca(PO_3)_2$, $Ca_2P_2O_7$, but, particularly, a hydroxyapatite crystal is preferable. Calcium phosphate crystals may be prepared according to a conventional method such as a wet method, a dry method, a hydrothermal method, an alkoxide method, or a flux method. For example, the hydroxyapatite crystal may be prepared by the following a wet method.

For example, in the case of hydroxyapatite, calcium hydroxide (or calcium carbonate) and phosphoric acid react in a solution at room temperature to 80° C., and the obtained nanocrystalline powders of hydroxyapatite are dried at 100° C. or less to obtain the hydroxyapatite crystal. More specifically, a white suspension insoluble in water, (i.e. slurry) may be obtained by mixing calcium hydroxide (or calcium carbonate) aqueous solution and a phosphoric acid aqueous solution. As the calcium hydroxide aqueous solution, a calcium hydroxide suspension in which calcium hydroxide is not completely dissolved may also be used. The phosphoric acid aqueous solution is added by drops so that, the pH of the reaction solution is preferably in the range of 7-11 and a tolerable range of pH is 1 or less, and the pH of the reaction solution is more preferably in the range of 7-9 and a tolerable range of pH is 0.5 or less. Furthermore, a calcium phosphate crystal suspension can be obtained by calcining the resulting suspension at 50° C.-1200° C. More particularly, a 0.6 mol/L of phosphoric acid aqueous solution (for example, 2 liters) is slowly added by drops to a 0.5 mol/L of the calcium hydroxide suspension (for example, 4 litters) until a pH of 7.5 is reached. The resulting suspension is calcined at 1200° C. for 30 minutes, after drying at 120° C. The synthesized hydroxyapatite can be confirmed whether it is a single phase by powder X-ray diffraction measurement.

The obtained calcium phosphate crystal suspension can be made into the calcium phosphate porous particles by a spray drying method. As conditions of the spray drying method, there may be mentioned, for example, a concentration of the suspension, an inlet temperature, a spray pressure, a flow rate of the sample, and the like. The calcium phosphate porous particle obtained by the spray drying method may be further calcined to obtain a calcined calcium phosphate porous particle. Calcination temperature is not particularly limited, but preferably 100-800° C., more preferably 100-400° C.

An average particle diameter of the calcium phosphate porous particle is not particularly limited, but preferably 0.1-300 µm, more preferably 1-100 µm, even more preferably 2.5-10 µm.

Particle size distribution of the calcium phosphate porous particle is not particularly limited, but preferably 0.01-3000 µm, more preferably 0.5-300 µm, even more preferably 1-20 µm.

Specific surface area by a BET method of the calcium phosphate porous particle is not particularly limited, but preferably 1-200 $m^2/g$, more preferably 40-150 $m^2/g$, even more preferably 60-120 $m^2/g$.

A pore volume of the calcium phosphate porous particle is not limited, but preferably 0.01-0.8 mL/g, more preferably 0.2-0.6 mL/g, even more preferably 0.4-0.45 mL/g.

As the average particle diameter, particle size distribution, specific surface area and pore volume of the calcium phosphate porous particle are in the above ranges, silver particles can be fixed in the grain boundary within the obtained silver-containing calcium phosphate sintered body.

(Reducing Agent)

The reducing agent used in the present invention is not limited, as long as the effect of the present invention can be achieved, but includes aldehyde, glucose, or hydroquinone.

Aldehyde, which is one of the reducing agents, is an organic compound having a structure in which one hydrogen atom bound to carbonyl carbon is substituted in the molecule. Aldehyde is represented by the general formula: R—CHO, and is composed of a carbonyl group, a hydrogen atom bonded to a carbon atom of the carbonyl group, and an arbitrary group (—R).

Specifically, aldehyde includes formaldehyde (HCHO), acetaldehyde ($CH_3CHO$), propionaldehyde ($C_2H_5CHO$), butanal ($C_3H_7CHO$), hexanal ($C_5H_{11}CHO$), glutaraldehyde ($C_5H_8O_2$), heptanal ($C_6H_{13}CHO$), octanal ($C_7H_{15}CHO$), nonanal ($C_8H_{17}CHO$), decanal ($C_9H_{19}CHO$), formic acid (HCOOH), acrolein (vinyl aldehyde, $CH_2$=CHCHO), benzaldehyde ($C_6H_5CHO$), cinnamaldehyde ($C_6H_5CH$=CHCHO), perillaldehyde ($C_9H_{13}CHO$), vanillin ($C_6H_3(OH)(OCH_3)CHO$), or glyoxal (($CHO)_2$), but formaldehyde (HCHO), acetaldehyde ($CH_3CHO$), propionaldehyde ($C_2H_5CHO$), acrolein (vinyl aldehyde, $CH_2$=CHCHO), or glutaraldehyde ($C_5H_8O_2$) is preferable.

In the step for application of reducing agent (1), the reducing agent is applied to the calcium phosphate porous particles.

The method for application of the reducing agent is not particularly limited, but there may be mentioned, for example, an dipping method wherein it is immersed in the solution containing the reducing agent, or a vapor deposition method wherein the reducing agent is evaporated and applied thereto In the dipping method, the reducing agent is applied to walls in the pores by immersing the calcium phosphate porous particle in the solution containing the reducing agent. For example, in the case of using aldehyde, a concentration of the aldehyde solution is not limited, as long as aldehyde may be applied to the pores, but preferably 0.001-10% by weight, more preferably 0.01-5% by weight, even more preferably 0.1-1% by weight. A temperature for applying aldehyde is not particularly limited, but preferably 0-80° C., more preferably 10-50° C. Further, a time for applying aldehyde is not particularly limited, but preferably 0.5-48 hours, more preferably 1-24 hours. Furthermore, the application of aldehyde is preferably conducted while stirring, but it is not thereto.

The concentration of the solution containing the reducing agent, temperature for applying aldehyde, time for applying aldehyde, and stirring can be suitably determined by those skilled in the art. For example, when the concentration of the solution containing the reducing agent is high, the amount of the reducing agent applied tends to increase. When the temperature is high, the amount of the reducing agent applied tends to increase. If time is extended, the amount of the reducing agent applied tends to increase. If stirring is conducted, the amount of the reducing agent applied tends to increase. Accordingly, those skilled in the art can conduct the dipping method by aptly combining the concentration of the solution containing the reducing agent, temperature, time, and stirring, in order to obtain the desired applying amount of the reducing agent.

In the vapor deposition method, the reducing agent is applied in the pores of the calcium phosphate porous particles by evaporating the reducing agent. More reducing agent can be applied to the pores of the calcium phosphate porous particle by using the vapor deposition method. For example, an aqueous solution containing the reducing agent is placed at a bottom of a vacuum desiccator, and the calcium phosphate porous particles are placed at a top of the desiccator. Then, the reducing agent can be vapor-deposited by reducing the pressure and allowing it to stand. For example, in the case of the use of aldehyde, a concentration of the aldehyde solution is not limited, as long as aldehyde may be applied to the pores, but preferably 0.01-25% by weight, more preferably 0.1-10% by weight, even more preferably 0.5-5% by weight. A temperature of vapor deposition is not particularly limited, but preferably 0-80° C., more preferably 10-60° C.

The concentration of the solution containing the reducing agent, temperature of vapor deposition, and time of vapor deposition can be suitably determined by those skilled in the art. For example, when the concentration of the solution containing the reducing agent is high, the deposition amount of the solution containing the reducing agent tends to increase. When the temperature is high, the deposition amount of the reducing agent tends to increase. If time is extended, the deposition amount of the reducing agent tends to increase. Accordingly, those skilled in the art can conduct the vapor deposition method by appropriately combining, the concentration of the solution containing the reducing agent, temperature, and time, in order to obtain the desired deposition amount of the reducing agent.

(2) Silver Precipitation Step

In the silver precipitation step (2), the calcium phosphate porous particles in which the reducing agent is applied, are immersed in the aqueous solution containing silver complex, to thereby obtain the silver particle-precipitated calcium phosphate porous particle (silver containing calcium phosphate porous particle).

(Aqueous Solution Containing Silver Complex)

The silver ion source used in the present invention is not particularly limited, but includes, for example, silver nitrate, silver bromide, or silver iodide. Further, a complexing agent is not particularly limited, but includes ammonia, sulfite, thiosulfate, or potassium iodide. The aqueous solution containing silver complex can be obtained by mixing them. In this case, a regulator such as sodium hydroxide may be used for pH adjustment.

For example, when the ammoniacal silver nitrate aqueous solution is used as the aqueous solution containing silver complex, it can be prepared according to conventional methods. In particular, an ammonia aqueous solution in which 25% aqueous ammonia (0.2 mL) is added to ultrapure water (50 mL), is prepared. Silver nitrate (0.175 g) is mixed with the ammonia aqueous solution to obtain the ammoniacal silver nitrate aqueous solution.

The pH of the ammoniacal silver nitrate aqueous solution is not limited, as long as it is alkaline, but preferably pH9.5-12, more preferably pH10-11.

Further, a concentration of silver contained in the ammoniacal silver nitrate aqueous solution is not limited, as long as silver reacts with an aldehyde group, but preferably 0.001-13 mol/L, more preferably 0.005-5 mol/L, even more preferably 0.02-0.5 mol/L.

The immersion temperature in the ammoniacal silver nitrate aqueous solution is not particularly limited, but preferably 0-80° C., more preferably 10-60° C. Further, time for immersion is not particularly limited, but preferably 0.1-24 hours, more preferably 1-12 hours. As they are in the above ranges, aldehyde applied to the calcium phosphate porous particles can react with silver ion, and thereby the simple substance silver can precipitate.

(3) Calcining Step

In the calcining step (3), the obtained the silver particle-precipitated calcium phosphate porous particle (silver-containing calcium phosphate porous particle) is calcined. A condition for calcining is not particularly limited, and thus the calcination can be conducted according to conventional methods in this field.

Calcination temperature is not particularly limited, as long as the effect of the present invention can be achieved, but preferably 800° C. or more, more preferably 900° C. or more, even more preferably 950° C. or more. The upper limit of the calcination temperature is not particularly limited, but preferably 1400° C. or less. As the calcination temperature is in the above ranges, silvers bound to the calcium phosphate porous particles are firmly fixed in the grain boundary as the silver particles. An atmosphere for calcining is not particularly limited, but the calcination is preferably conducted in the air. As the method for calcining, there may be mentioned calcination using an electric furnace.

As an embodiment in the calcining step, the silver particle-precipitated calcium phosphate porous particles (silver-containing calcium phosphate porous particles) may be molded and the resulting molded body may be calcined. For example, the silver particle-precipitated calcium phosphate porous particles (silver-containing calcium phosphate porous particles) are molded into prismatic shape, cylindrical shape, spherical shape, or the like by pressurization using a metallic mold or the like. The pressurization method is not particularly limited, there may be mentioned an uniaxial pressing method, a hot pressing method, a cold isostatic pressing method, an extrusion molding method, an injection molding method, a hot isostatic pressing method. The silver-containing calcium phosphate sintered bodies having various shapes can be obtained by calcining the resulting molded bodies. The sintered bodies with various shapes can be manufactured according to the shapes of antimicrobial materials used in various fields such as medical applications, household goods, photocatalysts, air conditioning materials, and the like.

As another embodiment in the calcining step, the silver particle-precipitated calcium phosphate porous particle (silver-containing calcium phosphate porous particle) may be calcined while pressure molding. Pressure molding and calcination can be conducted by hot pressing method or spark plasma sintering (SPS) method. In the hot pressing method, calcination is conducted in an electric furnace while molding under pressure.

On the other hand, the spark plasma sintering method is a solid compression sintering method wherein a mechanical pressurization and a pulse electric-current heating are directly applied to a material.

<<Implant Body>>

An implant body comprising the silver-containing calcium phosphate sintered body can be prepared by using the silver-containing calcium phosphate sintered body of the present invention or the silver-containing calcium phosphate sintered body obtained by the preparing method of the present invention. The implant body comprising the silver-containing calcium phosphate sintered body is, for example, a member implanted in a living bone and used for a portion directly contacting the living bone. As a method for preparing the implant body, known methods for preparing the implant body can be used without limit, except that the silver-containing calcium phosphate sintered body of the present invention is used.

<<Function>>

In the silver-containing calcium phosphate sintered body of the present invention, the mechanism by which silver particles are fixed to the grain boundary of calcium phosphate has not been fully elucidated, but is presumed to be as follows; (However, the present invention is by no means limited to the following explanation.)

Conventionally, in a silver mirror reaction in which silver is precipitated, glass or the like for precipitating silver is placed in a solution obtained by adding aldehyde to an ammoniacal silver nitrate aqueous solution, and then silver is precipitated on the glass by applying heat. The present inventors attempted to fix silver particles to grain boundaries of calcium phosphate sintered particles by immersing calcium phosphate porous particles in the solution obtained by adding aldehyde to an ammoniacal silver nitrate aqueous solution. However, in this method, the silver particles adhered to the outside of the calcium phosphate sintered particles and could not be fixed to the grain boundaries.

In the present invention, the reducing agent (such as aldehyde) is initially applied to the pores of the calcium phosphate porous particles, and the calcium phosphate porous particles to which the reducing agent is applied are immersed in an aqueous solution containing a silver complex (such as ammoniacal silver nitrate aqueous solution), and whereby it is considered that the silver complex can be bound to the reducing agent applied to the pores and can be precipitated. Then, it is considered that the calcium phosphate sintered particles in which silver particles are fixed at grain boundaries can be obtained by calcining the silver particle-precipitated calcium phosphate porous particles (silver-containing calcium phosphate porous particles). In the conventional silver mirror reaction using the solution obtained by adding a reducing agent (aldehyde) to the ammoniacal silver nitrate aqueous solution, it is considered that adhesion of the reducing agent (aldehyde) to the pores does not occur, and therefore silver particles cannot be fixed to the grain boundaries.

[3] Method of Raman Spectroscopic Analysis Using Silver-Containing Calcium Compound Porous Particle Raman spectroscopic analysis of a substance to be tested can be conducted using the silver-containing calcium compound porous particle. Raman spectroscopic analysis can be conducted with high sensitivity, by using the silver-containing calcium compound porous particles.

<<Silver-Containing Calcium Compound Porous Particle>>

The silver-containing calcium compound porous particle of the present invention contains silver particles on a surface and inside (porous).

The average particle diameter of the silver particle is not limited as long as the effect of the present invention can be achieved. However, the average particle diameter of the silver particle is preferably 10-500 nm (0.01-0.5 μm). That is to say, the upper limit of the average particle diameter is preferably 0.5 μm or less, more preferably 0.25 μm or less. The lower limit of the average particle diameter is preferably 0.01 μm or more, more preferably 0.05 μm or more, even preferably 0.1 μm or more. As the average particle diameter is in the above range, Raman spectroscopic analysis can be conducted with high sensitivity.

The average particle diameter of the silver-containing calcium compound porous particle is not particularly limited. However, the upper limit of the average particle diameter is preferably 300 μm or less, more preferably 100 μm or less, even more preferably 40 μm or less. The lower limit of the average particle diameter is preferably 0.1 μm or more, more preferably 1 μm or more, even more preferably 2.5 μm or more, most preferably 4 μm or more.

Further, the diameter (particle size) of the silver-containing calcium compound porous particle is not particularly limited, but preferably 0.01-3000 μm, more preferably 0.5-300 μm, even more preferably 1-20 μm.

A particle size distribution of the silver-containing calcium compound porous particle is not particularly limited, but preferably 0.01-3000 μm, more preferably 0.5-300 μm, even more preferably 1-20 μm.

A specific surface area by a BET method of the silver-containing calcium compound porous particle is not particularly limited, but preferably 1-200 $m^2/g$, more preferably 10-150 $m^2/g$, even more preferably 20-120 $m^2/g$.

A pore volume of the silver-containing calcium compound porous particle is not limited, but preferably 0.01-0.8 mL/g, more preferably 0.05-0.6 mL/g, even more preferably 0.1-0.45 mL/g.

As the average particle diameter, the particle size distribution, the specific surface area and the pore volume of the silver-containing calcium compound porous particle are in the above ranges, it is possible to perform Raman spectroscopic analysis efficiently.

The amount of the silver particles in the silver-containing calcium compound porous particle is not particularly limited. However, the lower limit of the amount of the silver particles is preferably 0.03% by weight or more, more preferably 0.1% by weight or more, more preferably 1% by weight or more, even more preferably 5% by weight or more, most preferably 7% by weight or more. The upper limit of the amount of the silver particles is also limited, but preferably 40% by weight or less, more preferably 30% by weight or less, more preferably 20% by weight or less, even more preferably 15% by weight or less, most preferably 11% by weight or less. As the amount of the silver particles is in the above range, it is possible to perform Raman spectroscopic analysis efficiently.

The calcium compound is not limited, but includes calcium phosphate, calcium carbonate, calcium sulfate, or calcium oxide. Calcium phosphate is not particularly limited, but includes hydroxyapatite, calcium dihydrogen phosphate, calcium dihydrogen phosphate hydrate, calcium monohydrogen phosphate, calcium monohydrogen phosphate hydrate, octacalcium phosphate, or tricalcium phosphate. In the case of calcium phosphate, the calcium phosphate porous particle and the silver-containing calcium phosphate porous particle described in the above item: "[1] Method for Preparing Silver-containing Calcium Phosphate sintered body" are obtained. Calcium carbonate is a compound represented by $CaCO_3$, $CaCO_3.2H_2O$, or $CaCO_3.6H_2O$. Calcium sulfate is a compound represented by $CaSO_4$, $CaSO_4.2H_2O$, or $CaSO_4.1/2H_2O$. Calcium oxide is a compound represented by CaO.

<<Method for Preparing Silver-Containing Calcium Compound Porous Particles>>

The method for preparing the silver-containing calcium compound porous particles of the present invention comprises the steps of (1) applying a reducing agent to calcium compound porous particle, and (2) immersing the reducing agent-applied calcium compound porous particles in an aqueous solution containing silver complex to precipitate silver particles on a surface of particles constituting the calcium compound porous particles.

Specifically, the method for preparing the silver-containing calcium phosphate porous particles of the present invention comprises the steps of (1) applying a reducing agent to calcium phosphate porous particles, and (2) immersing the reducing agent-applied calcium phosphate porous particles in an aqueous solution containing silver complex to precipitate silver particles on a surface of particles constituting the calcium phosphate porous particles.

That is to say, the silver-containing calcium compound porous particles (for example, silver-containing calcium phosphate porous particles) can be prepared by carrying out the step for application of reducing agent (1) and the silver precipitation step (2) in above item "method for preparing silver-containing calcium phosphate sintered body" of the present invention. The step for application of reducing agent (1) and the silver precipitation step (2) in the method for preparing silver-containing calcium compound porous particles is basically the same as the step for application of reducing agent (1) and the silver precipitation step (2) in the method for preparing silver-containing calcium phosphate sintered body.

In the case where the calcium compound is calcium carbonate, calcium sulfate or calcium oxide, silver containing calcium carbonate porous particles, silver-containing calcium sulfate porous particles, or silver-containing calcium oxide porous particles can be obtained by using calcium carbonate porous particles, calcium sulfate porous particles or calcium oxide porous particles respectively, instead of calcium phosphate porous particles.

(Preparation of Calcium Carbonate Porous Particles)

The calcium carbonate porous particles can be prepared as follows. For example, a sodium bicarbonate ($NaHCO_3$) aqueous solution with a trace amount of phosphoric acid ($H_3PO_4$) is prepared, and it is added to a calcium chloride ($CaCl_2$) aqueous solution and the whole is mixed. As a result, spherical calcium carbonate porous particles can be precipitated.

(Preparation of Calcium Sulfate Porous Particles)

The calcium sulfate porous particles can be prepared as follows. For example, a solution of calcium chloride ($CaCl_2$) and sodium salt of ethylenediaminetetraacetic acid is prepared at 95° C. using a solvent of ethylene glycol and water. Further, a solution of ammonium sulfate (($NH_4)_2SO_4$) and sodium salt of ethylenediaminetetraacetic acid is prepared at 95° C., and these two solutions are mixed. As a result, spherical calcium sulfate porous particles can be precipitated.

(Preparation of Calcium Oxide Porous Particles)

The calcium oxide porous particles can be prepared as follows. For example, calcium carbonate porous particles are calcined at a temperature of 600° C. or more to desorb carbon dioxide, as a result calcium oxide porous particles can be prepared.

In the silver-containing calcium compound porous particle of the present invention, silver is contained in porous particles containing calcium. Therefore, by using it as a carrier (substrate) of a sample, Raman spectroscopic analysis can be measured with high sensitivity. In particular, it is preferable that the calcium compound contains phosphoric acid.

<<Method of Raman Spectroscopic Analysis>>

The Raman spectroscopic analysis of the substance to be tested can be performed by using the silver-containing calcium compound porous particle of the present invention. In the present invention, the method of Raman spectroscopic analysis can be conducted according to the apparatus and procedures (conditions) used for conventional methods of Raman spectroscopic analysis, except that the silver-containing calcium compound porous particles are used.

When a substance is irradiated with monochromatic light of frequency Vi and scattered, Raman lines of Stokes line and anti-Stokes line appears due to Raman effect. The Raman spectroscopic analysis is a method for analyzing substances utilizing the above phenomenon. By measuring the wavelength and scattering intensity (Raman spectrum) of the Raman line, it is possible to measure the energy level of the substance, identify the substance, quantify the substance, and the like.

For the measurement of Raman spectroscopy, a Raman spectrophotometer having a light source, a sample irradiation part, a spectroscope, and a scattering light detector is used.

(Test Substance-Application Step)

The method of Raman spectroscopic analysis of the present invention comprises the steps of applying a substance to be tested (test substance) to the silver-containing calcium compound porous particles (hereinafter, sometimes referred to as test substance-application step (1))

The method of application of the test substance is not particularly limited as long as Raman scattering light can be measured, but the test substance can be applied thereto by immersion of the silver-containing calcium compound porous particles into the liquid containing the substance. Further, the test substance can be applied thereto by placing the liquid containing the test substance onto the silver-containing calcium compound porous particles.

The immersion into the liquid containing the test substance is not particularly limited as long as the substance applies to the silver-containing calcium compound porous particle. The concentration of the test substance in the liquid is not particularly limited, but preferably $1 \times 10^{-9}$ mol/L or more. The liquid used for immersion or placement is not particularly limited, but for example, there may be mentioned a sodium chloride solution, a phosphate buffer solution, a carbonate buffer solution, serum, blood, mucosal fluid, or the like. Further, serum, blood, mucosal fluid or the like can be measured directly or by diluting it in buffer.

(Laser Light-Irradiation Step)

The method of Raman spectroscopic analysis of the present invention comprises the steps of (2) irradiating the substance-applied, silver-containing calcium compound porous particles with laser light (hereinafter, sometimes referred to as laser light-irradiation step (2))

Laser light irradiation conditions such as laser wavelength (excitation wavelength), power, exposure time, average frequency, and the like can be appropriately determined depending on the test substance. A short wavelength is basically selected for the laser light wavelength, but for example, when fluorescence is generated, a long wavelength laser may be used. The laser power is preferably as strong as possible, so long as it does not damage the test substance. The exposure time may be set to a time that allows sufficient Raman spectrum intensity to be obtained according to the laser power.

(Scattering Light Detection Step)

The method of Raman spectroscopic analysis of the present invention comprises the steps of (3) detecting a Raman scattering light (hereinafter, sometimes referred to as detection step (3)).

As a detector for Raman scattering light, a photomultiplier tube or a CCD detector may be used. A weak scattering light can be detected by using these instruments.

<<Function>>

The mechanism by which Raman spectroscopic analysis may be analyzed with high sensitivity by using the silver-containing calcium compound porous particles of the present invention has not been fully elucidated, but is presumed to be as follows; (However, the present invention is by no means limited to the following explanation.)

Since the matrix is a calcium compound having an excellent adsorption property, the test substance is easily adsorbed onto the surface and a trace amount of the test substance may adsorb to the calcium compound surface and concentrated thereon, as a result, Raman spectroscopic analysis may be performed. That is, due to the excellent adsorption property of the calcium compound, an extremely low concentration of the test substance can be collected in larger amounts on the surface of the silver nanoparticles, so that Raman scattering light can be enhanced.

EXAMPLES

The present invention now will be further illustrated by, but is by no means limited to, the following Examples.

Preparation Example

In this preparation example, porous particles of hydroxyapatite were prepared.

(1) Synthesis of Hydroxyapatite Nanocrystal

Calcium carbonate ($CaCO_3$) was calcined at 1050° C. for 3 hours to obtain calcium oxide (CaO). Then, a triple amount of purified water divided into three equal parts was added thereto and it was hydrolyzed to obtain calcium hydroxide. Hydroxyapatite nanocrystals were synthesized by adding dropwise 0.3 mol/L of aqueous phosphoric acid ($H_3PO_4$) solution (2 L) to calcium hydroxide ($Ca(OH)_2$) suspension (2 L) adjusted to 0.5 mol/L. The final pH of the reacted suspension was adjusted to 8.0, and the suspension was suction-filtered, dried at 100° C. and calcined at 1200° C. Then, single phase of hydroxyapatite was confirmed by powder X-ray diffraction measurement.

(2) Preparation of Hydroxyapatite Porous Particle

Figure 2:
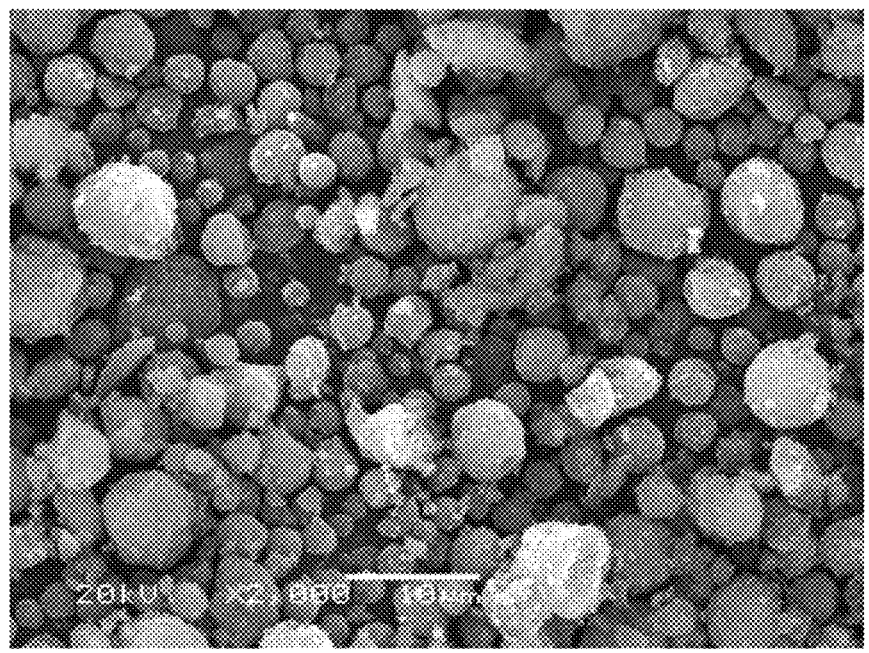
FIG. 2 is a photograph showing hydroxyapatite porous particles as a raw material of the silver-containing calcium phosphate sintered body.

Porous particles were prepared from the resulting hydroxyapatite nanocrystal suspension using a spray dryer (Mini Spray Dryer B-290, Buchi). 180-185° C. of an inlet temperature, aspirator of 75, and Q-Flow of 30 are set. Further, 60 to 70° C. of an outlet temperature and a pump speed of 20 were set. The prepared hydroxyapatite particles had an average particle diameter of 5 µm and a particle size distribution of 1 to 20 µm. Further, according to the BET measurement, the specific surface area was 88 $m^2/g$ and the pore volume was 0.44 mL/g. The obtained particles are referred to as HAp-60. The HAp-60 was further calcined at 400° C., 600° C., 800° C., or 1000° C. Hydroxyapatite particles calcined at 800° C. had a specific surface area of 45 $m^2/g$ and a pore volume of 0.13 mL/g. Samples calcined at 400° C., 600° C., 800° C., and 1000° C. are referred to as HAp-400, HAp-600, HAp-800, and HAp-1000, respectively. The appearance of HAp-60 is shown in FIG. 2.

Example 1

In this Example, formaldehyde was applied to hydroxyapatite porous particles by dipping method to prepare silver-containing hydroxyapatite porous particles, and by calcining them, silver-containing calcium phosphate sintered particles (silver-containing calcium phosphate sintered body) were prepared.

Figure 3:
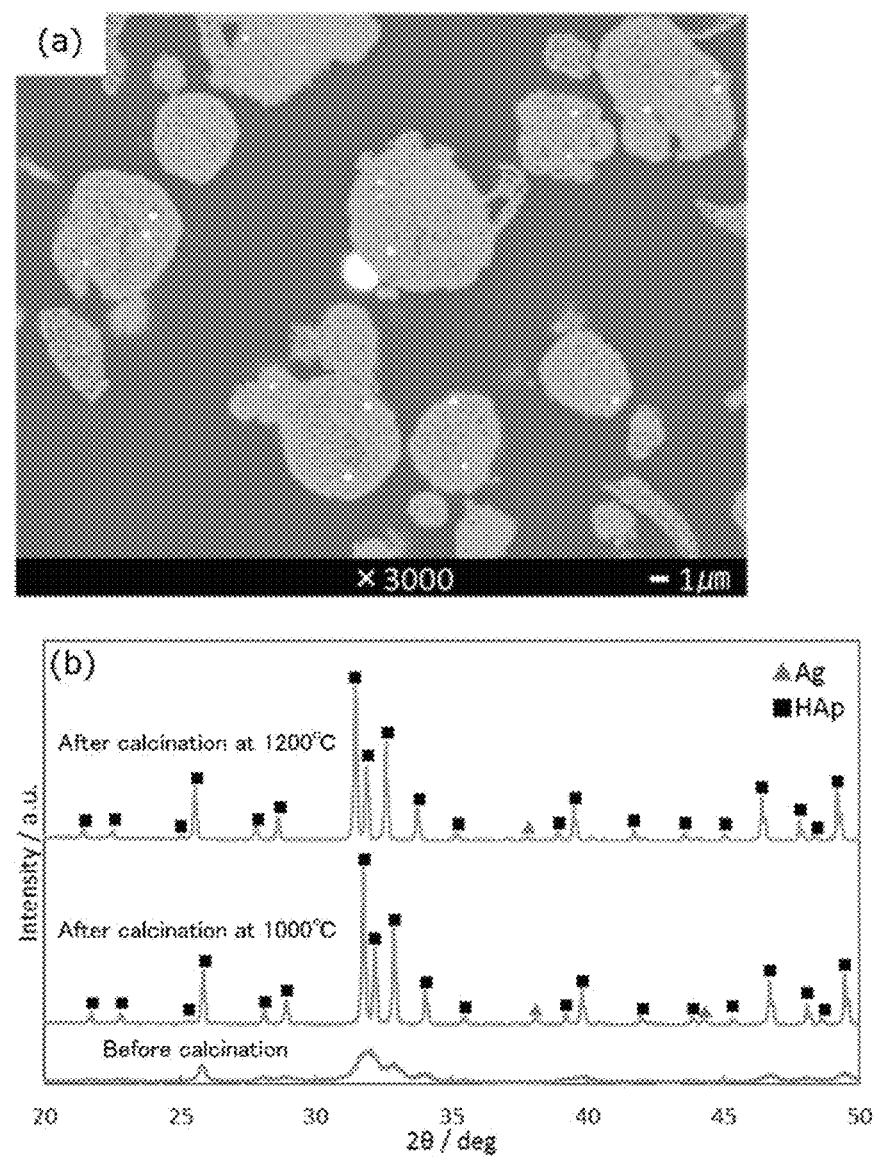
FIG. 3 is a photograph (a) and an X-ray diffraction pattern (b) of the silver-containing calcium phosphate sintered particles prepared by using the hydroxyapatite porous particles to which formaldehyde is applied by dipping method (Example 1).

5.0 g of HAp-60 obtained in Preparation Example was added to 0.037% by weight of formaldehyde ($H_2C=O$) aqueous solution (pH4.3:250 mL), and the whole was stirred for 3 hours at room temperature. Solids were separated from liquid by centrifugation at 3000 rpm for 10 minutes. An ammoniacal silver nitrate aqueous solution (pH11.15) was prepared by adding 0.875 g of silver nitrate ($AgNO_3$) to a solution obtained by adding 25% aqueous ammonia (1 mL) to ultrapure water (250 mL). This ammoniacal silver nitrate aqueous solution was added to the hydroxyapatite porous particles separated from liquid, and further the whole was stirred for 3 hours for reaction. Solids were separated from liquid by centrifugation at 3000 rpm for 10 minutes, and further the particles were washed twice with the addition of ultrapure water. The silver-containing hydroxyapatite porous particles vacuum-dried at 60° C. were calcined at 1000° C. for 3 hours or calcined at 1200° C. for 30 minutes to obtain silver-containing hydroxyapatite sintered particles. In silver-containing HAp-60 before calcination, no simple substance of silver diffraction line was observed, but diffraction line of simple substance of silver was observed at 38.1 degrees by calcining (FIG. 3b).

<<Measurement of Silver Particles Distribution>>

The internal structure of the silver-containing hydroxyapatite sintered particles obtained in Example 1 was observed. The silver-containing hydroxyapatite sintered particles obtained by calcining silver-containing HAp-60 at 1000° C. for 3 hours were embedded in a resin and the particle cross-section was exposed by an ion sputtering. The particle cross-section was observed with a backscattered electron image of the scanning electron microscope. White particles derived from silver were observed inside the particles (FIG. 3a).

Example 2

In this Example, formaldehyde was applied to hydroxyapatite porous particles by dipping method to prepare silver-containing hydroxyapatite porous particles, and by calcining them, silver-containing calcium phosphate sintered particles (silver-containing calcium phosphate sintered body) were prepared.

The procedure of Example 1 was basically repeated by using the HAp-60 as the hydroxyapatite porous particles, to obtain the silver-containing calcium phosphate sintered particles, except that 1.0% by weight of formaldehyde aqueous solution was used instead of 0.037% by weight of formaldehyde aqueous solution, and it was stirred for 24 hours at room temperature instead of the stirring for 3 hours at room temperature.

In particular, 1.0 g of HAp-60 was added to 1.0% by weight of formaldehyde aqueous solution (pH3.3), and the whole was stirred for 24 hours at room temperature. Solids were separated from liquid by centrifugation at 3000 rpm for 10 minutes. An ammoniacal silver nitrate aqueous solution (pH11.34) was prepared by adding 0.175 g of silver nitrate ($AgNO_3$) to a solution obtained by adding 25% aqueous ammonia (0.2 mL) to ultrapure water (50 mL). The ammoniacal silver nitrate aqueous solution was added to the hydroxyapatite porous particles separated from liquid, and further the whole was stirred for 3 hours for reaction. Solids were separated from liquid by centrifugation at 3000 rpm for 10 minutes, and further the particles were washed twice with the addition of ultrapure water. The silver-containing hydroxyapatite porous particles vacuum-dried at 60° C. were calcined at 1200° C. for 30 minutes to obtain silver-containing hydroxyapatite sintered particles.

Figure 4:
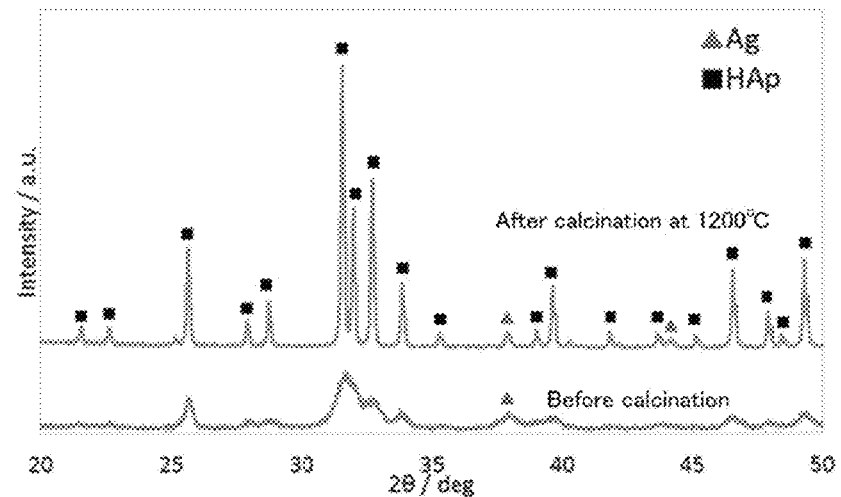
FIG. 4 is an X-ray diffraction pattern of the silver-containing calcium phosphate sintered particles prepared by using the hydroxyapatite porous particles to which formaldehyde is applied by dipping method (Example 2).

The powder X-ray diffraction patterns before and after calcining are shown in FIG. 4. The diffraction lines of simple substance of silver were observed before and after calcining.

Comparative Example 1

In this Comparative Example, the silver-containing calcium phosphate sintered particles (silver-containing calcium phosphate sintered body) were prepared using an acetic acid aqueous solution instead of the aldehyde aqueous solution.

1.0 g of HAp-60 was added to the acetic acid aqueous solution (pH4.3), and the whole was stirred for 3 hours at room temperature. Solids were separated from liquid by centrifugation at 3000 rpm for 10 minutes. An ammoniacal silver nitrate aqueous solution (pH11.34) was prepared by adding 0.175 g of silver nitrate ($AgNO_3$) to a solution obtained by adding 25% aqueous ammonia (0.2 mL) to ultrapure water (50 mL). The ammoniacal silver nitrate aqueous solution was added to the hydroxyapatite porous particles separated from liquid, and further the whole was stirred for 3 hours for reaction. Solids were separated from liquid by centrifugation at 3000 rpm for 10 minutes, and further the particles were washed twice with the addition of ultrapure water. The silver-containing hydroxyapatite porous particles vacuum-dried at 60° C. were calcined at 1000° C. for 3 hours or calcined at 1200° C. for 30 minutes to obtain silver-containing hydroxyapatite sintered particles.

Figure 5:
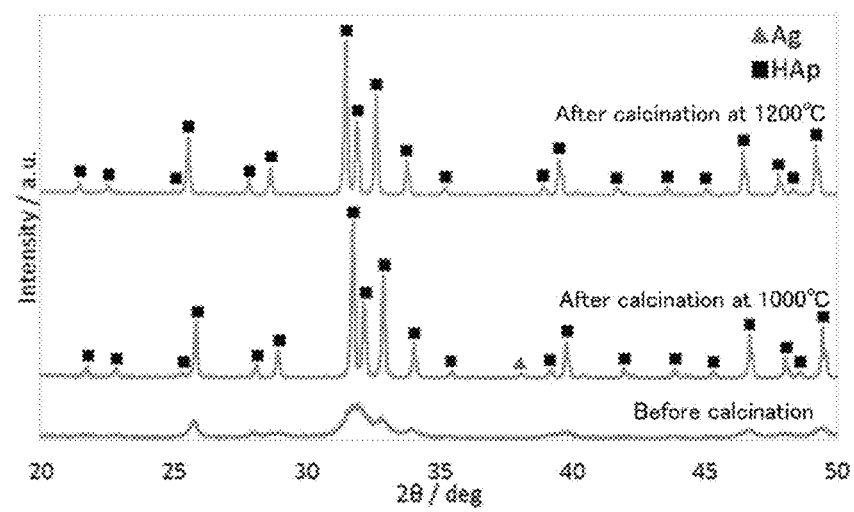
FIG. 5 is an X-ray diffraction pattern of the calcium phosphate sintered particle to which silver is bound by using an acetic acid aqueous solution and an ammoniacal silver nitrate aqueous solution (Comparative Example 1).

The powder X-ray diffraction patterns before and after calcining are shown in FIG. 5. A slight diffraction line of simple substance of silver was observed in the silver-containing hydroxyapatite sintered particles calcined at 1000° C., but diffraction line of simple substance of silver was not observed in silver-containing hydroxyapatite sintered particles calcined at 1200° C. In addition, since silver nitrate reacted on the surface of the particles, silver particles were formed on the outer surface of the particles.

Comparative Example 2

In this Comparative Example, the silver-containing calcium phosphate sintered particles (silver-containing calcium phosphate sintered body) were prepared using a silver nitrate aqueous solution.

Figure 6:
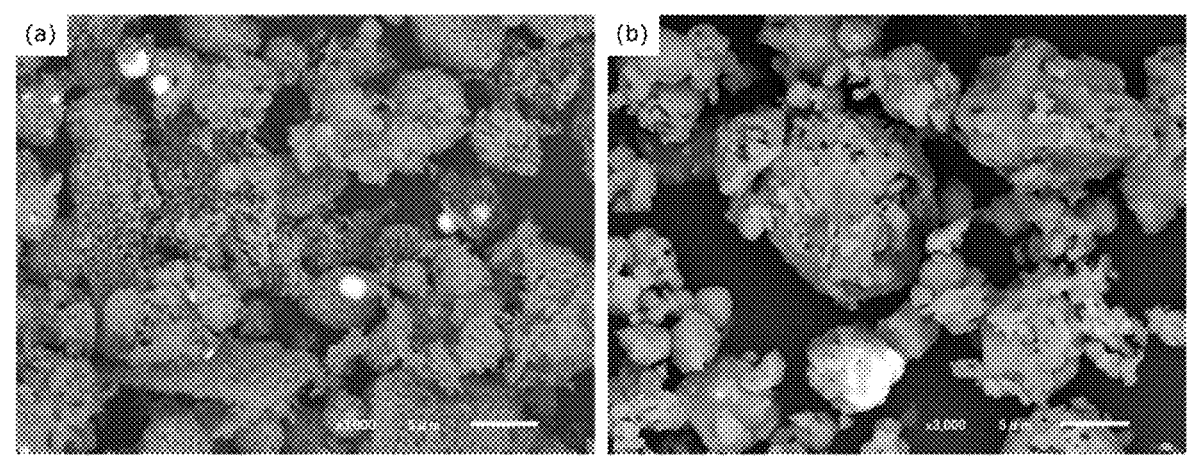
FIG. 6 is an image from a backscattered electron microscope of particles obtained by sintering, at 1000° C. (a) or 1200° C. (b), the hydroxide apatite sintered particles (vacuum drying) to which silver is bound by using the silver nitrate aqueous solution (Comparative Example 2).

0.175 g of silver nitrate ($AgNO_3$) was dissolved in 50 mL of ultrapure water (pH5.2), and 1.0 g of HAp-60 or HAp-800 was added thereto, and the whole was stirred for 6 hours at room temperature. Solids were separated from liquid by centrifugation at 3000 rpm for 10 minutes, and further the particles were washed twice with the addition of ultrapure water, to obtain the silver-containing calcium phosphate porous particles. They were vacuum-dried at 60° C. and calcined at 1000° C. for 3 hours or at 1200° C. for 30 minutes. According to the powder X-ray diffraction patterns before and after calcining, a diffraction line of silver phosphate ($Ag_3PO_4$) was observed in silver-containing HAp-60 before calcining, and, after calcining, diffraction lines of tricalcium phosphate, hydroxyapatite, and simple substance of silver were observed respectively. On the other hand, a diffraction line of silver phosphate ($Ag_3PO_4$) was detected in silver-containing HAp-800 before calcining, and, after calcining, slight diffraction lines of tricalcium phosphate and simple substance of silver were detected. This is because it is considered that part of hydroxyapatite was dissolved due to the acidity of the aqueous silver nitrate solution and silver phosphate was precipitated. While, when calcined, silver phosphate was not detected because silver phosphate was converted to simple substance of silver. In addition, silver phosphate reacted on the surface of the particles to form silver particles on the outer surface of the particles, but silver particles were not formed inside the hydroxyapatite sintered particles (FIG. 6). Furthermore, the sample prepared by this method does not maintain its shape because hydroxyapatite dissolved in an acidic solution.

Comparative Example 3

In this Comparative Example, the silver-containing calcium phosphate sintered particles (silver-containing calcium phosphate sintered body) were prepared using a silver nitrate aqueous solution.

The procedure of Comparative Example 2 was repeated to obtain the silver-containing calcium phosphate sintered particles, except that centrifugation and washing with ultrapure water were not carried out and that freeze-drying was carried out instead of vacuum drying.

Figure 7:
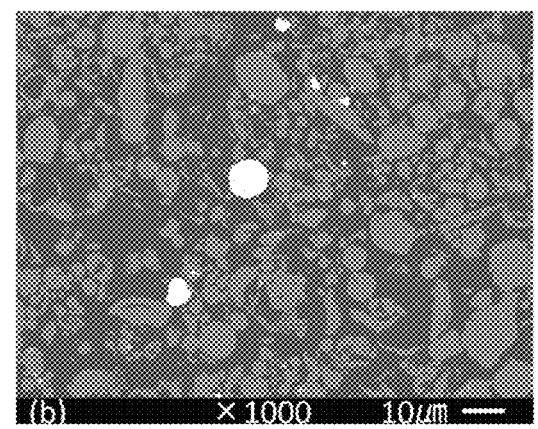
FIG. 7 is a backscattered electron microscopic image of the hydroxide apatite sintered particles (freeze dry) to which silver is bound by using the silver nitrate aqueous solution (Comparative Example 3).

Specifically, 0.175 g of silver nitrate ($AgNO_3$) was dissolved to 50 mL of ultrapure water (pH5.2), and 1.0 g of HAp-60 were added thereto, and the whole was stirred for 6 hours at room temperature. They were freeze-dried at −20° C. and calcined at 1000° C. for 3 hours or at 1200° C. for 30 minutes. The photograph of silver-containing HAp-60 calcined at 1200° C. is shown in FIG. 7. Silver phosphate reacted on the surface of the particles to form silver particles on the outer surface of the particles, but silver particles were not formed inside the hydroxyapatite sintered particles.

Comparative Example 4

In this Comparative Example, the silver-containing calcium phosphate sintered particles (silver-containing calcium phosphate sintered body) were prepared using a silver phosphate aqueous solution.

0.0487 g of disodium hydrogenphosphate aqueous solution (1 mL) was added to 0.175 g of silver nitrate aqueous solution (9 mL). After stirring at room temperature, a solid phase was centrifuged (3000 rpm, 10 minutes), and washed by ultrapure water. It was suspended in 50 mL of ultrapure water, and 1.0 g of HAp-60 or HAp-800 was added thereto, and the whole was stirred for 6 hours at room temperature. Furthermore, a solid phase was separated by centrifugation, vacuum-dried at 60° C., and calcined at 1000° C. for 3 hours or 1200° C. for 3 hours. Silver phosphate reacted on the surface of the particles to form silver particles on the outer surface of the particles, but silver particles were not formed inside the hydroxyapatite sintered particles.

Comparative Example 5

In this Comparative Example, the silver-containing calcium phosphate sintered particles (silver-containing calcium phosphate sintered body) were prepared using silver colloidal particles.

Figure 8:
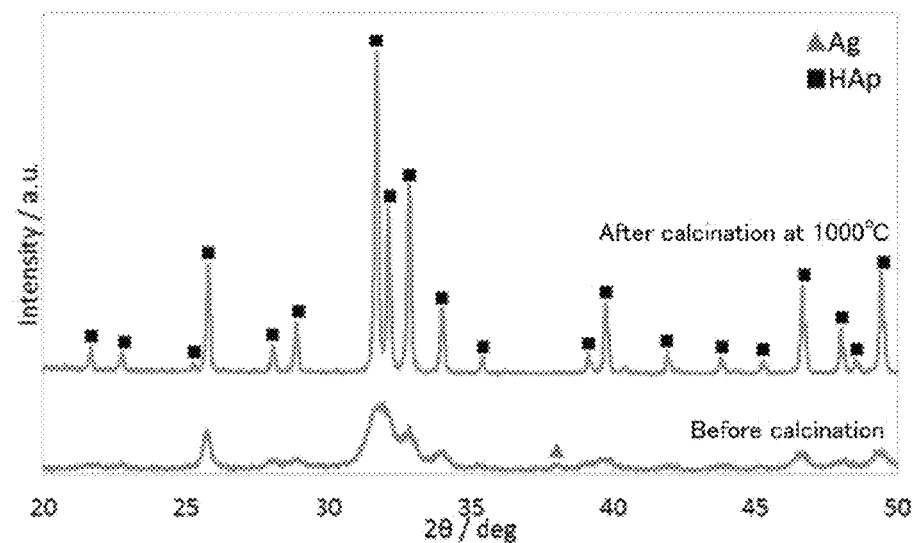
FIG. 8 is an X-ray diffraction pattern of the calcium phosphate sintered particles to which silver is bound by using silver colloidal particles (Comparative Example 5).

1.0% of sodium citrate aqueous solution (40 mL) was added to 0.018% of silver nitrate aqueous solution (2.0 L) and the whole was stirred for 2 hours in a constant temperature bath at 70° C. After changing the solution to yellow (particle size: 33 nm), solid was separated from liquid at a rotation speed of 12000 rpm for 2 hours, and washed. Then, the silver colloidal particles were dispersed in 400 mL of ultrapure water, and 2.0 g of HAp-60 or HAp-800 was added thereto, and the mixture was stirred at room temperature for 6 hours. Further, a solid phase was separated by centrifugation, and vacuum-dried at 60° C. A part of them was calcined at 1000° C. for 3 hours or 1200° C. for 30 minutes. The HAp-60 reacted with the silver colloidal particles was gray, but the powder changed to white upon calcination. The HAp-800 was light gray and changed to white upon calcination. Powder X-ray diffraction patterns of the HAp-60 before and after calcining at 1000° C. are shown in FIG. 8. The diffraction line of simple substance of silver was observed before calcination, but was not observed after calcination because silver was evaporated. Further, the silver content was low in both HAp-60 and HAp-800. Furthermore, no silver particles were formed inside the hydroxyapatite sintered particles.

Example 3

In this Example, glutaraldehyde was applied to hydroxyapatite porous particles by the vapor deposition method to prepare silver-containing hydroxyapatite porous particles, and by calcining them, silver-containing calcium phosphate sintered particles (silver-containing calcium phosphate sintered body) were prepared.

5 mL of glutaraldehyde aqueous solution (10%) was placed at a bottom of a vacuum desiccator and 1.0 g of HAp-60 or HAp-800 was placed therein, and then, the vacuum desiccator was depressurized and allowed to stand at 37° C. for 24 hours. Subsequently, 0.175 g of silver nitrate was added to a solution obtained by adding 25% aqueous ammonia (0.2 mL) to ultrapure water (50 mL), and the whole was stirred for 3 hours at room temperature. Under the same conditions as above, the solid phase was separated by centrifugation and washed twice with ultrapure water to obtain hydroxyapatite porous particles (silver-containing hydroxyapatite porous particles) in which silver particles were precipitated. They were vacuum-dried at 60° C., and then calcined at 1200° C. for 30 minutes.

Example 4

In this Example, glutaraldehyde was applied to hydroxyapatite porous particles by the vapor deposition method to prepare silver-containing hydroxyapatite porous particles, and by calcining them, silver-containing calcium phosphate sintered particles (silver-containing calcium phosphate sintered body) were prepared.

Figure 9:
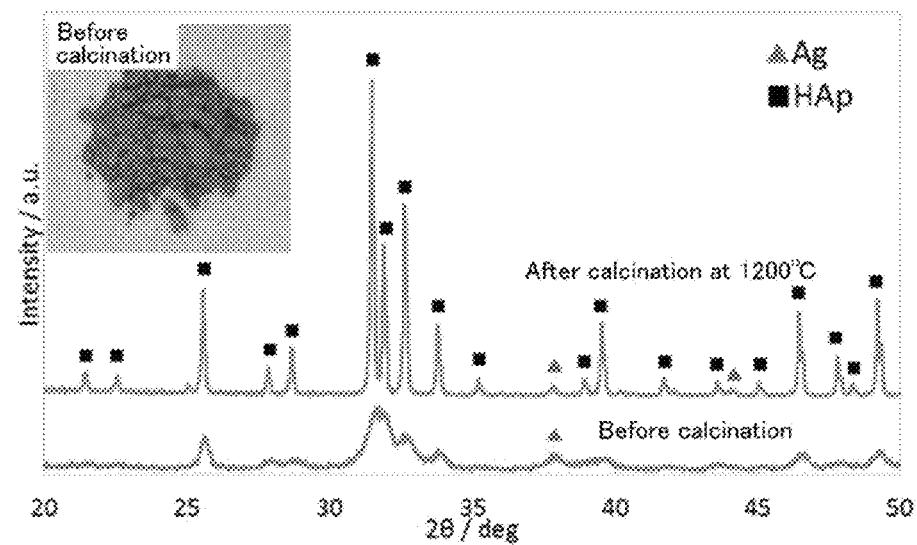
FIG. 9 is an appearance and an X-ray diffraction pattern of the silver-containing calcium phosphate sintered particles prepared by using the hydroxyapatite porous particles to which glutaraldehyde is applied by vapor deposition method (Example 4).

The procedure of Example 3 was repeated to obtain silver-containing hydroxyapatite sintered particles except that the temperature at which the hydroxyapatite porous particles were reacted with the ammoniacal silver nitrate aqueous solution was changed to 50° C. Simple substance of silver was detected by powder X-ray diffraction measurement (FIG. 9). The appearance of silver-containing hydroxyapatite porous particles before calcining is shown in FIG. 9. The amount of silver contained in the silver-containing hydroxyapatite sintered particles could be increased by raising the temperature of the silver mirror reaction with glutaraldehyde.

Example 5

In this Example, formaldehyde was applied to hydroxyapatite porous particles by the vapor deposition method to prepare silver-containing hydroxyapatite porous particles, and by calcining them, silver-containing calcium phosphate sintered particles (silver-containing calcium phosphate sintered body) were prepared.

Figure 10:
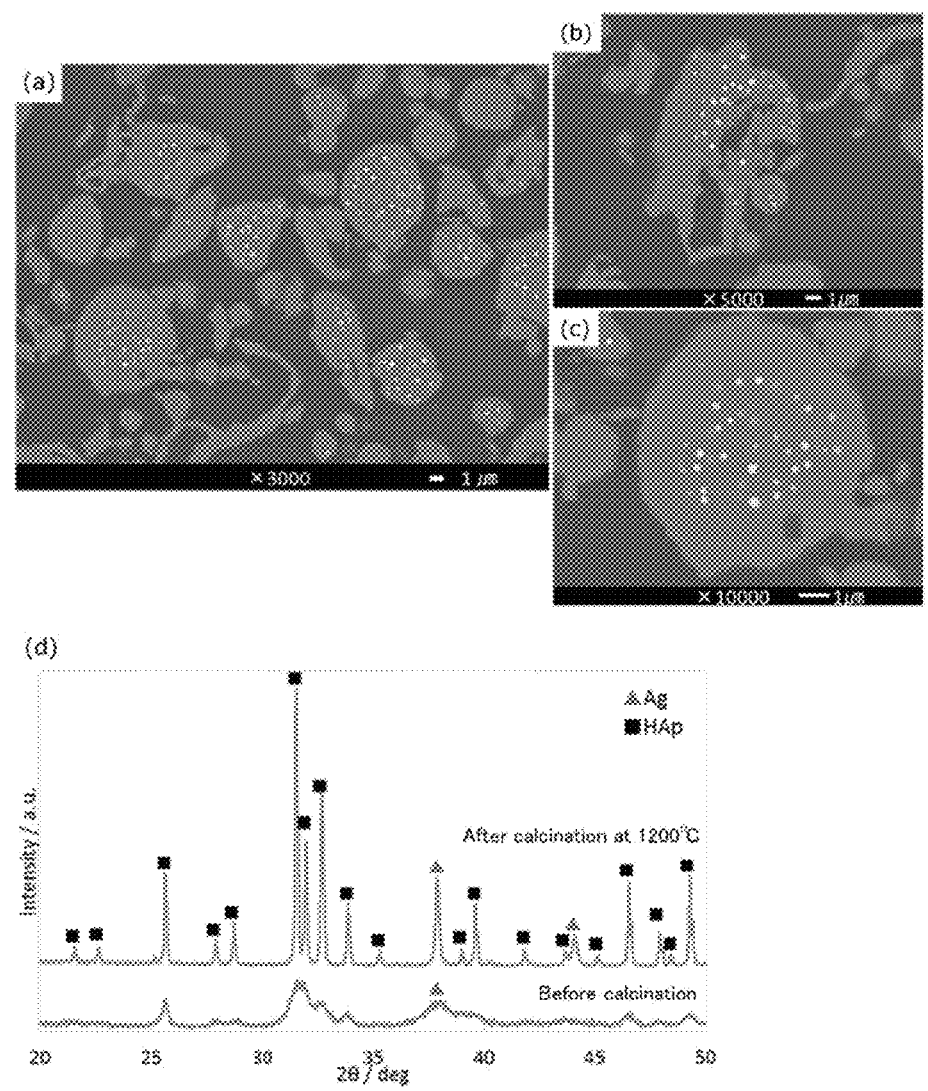
FIG. 10 is an image from a backscattered electron microscope and an X-ray diffraction pattern of the silver-containing calcium phosphate sintered particles prepared by using the hydroxyapatite porous particles to which formaldehyde is applied by a vapor deposition method (Example 5).

The procedure of Example 3 was repeated to prepare silver-containing hydroxyapatite porous particles, and then by calcining them, to obtain silver-containing calcium phosphate sintered particles, except that 10% of formaldehyde aqueous solution was used instead of 10% of glutaraldehyde aqueous solution Specifically, 5 mL of formaldehyde aqueous solution (10%) was placed at a bottom of a vacuum desiccator and 1.0 g of HAp-60 or HAp-800 was placed therein, and then, the vacuum desiccator was depressurized and allowed to stand at 37° C. for 24 hours. Subsequently, 0.175 g of silver nitrate was added to a solution obtained by adding 25% aqueous ammonia (0.2 mL) to ultrapure water (50 mL), and the whole was stirred for 3 hours. Under like conditions as above, the solid phase was separated by centrifugation and washed twice with ultrapure water. They are vacuum-dried at 60° C., and calcined at 1200° C. for 30 minutes. As shown in FIG. 10a to c. A large number of silver particles were fixed inside the resulting silver-containing hydroxyapatite sintered particles. Further, in silver-containing HAp-60, a clear diffraction line of simple substance of silver was observed even before calcining, and when it was calcined at 1200° C., simple substance of silver with good crystallinity was detected (FIG. 10d). Furthermore, no other crystals such as tricalcium phosphate were observed even after calcining.

<<Shape of Silver Particles and Hydroxyapatite within Silver-Containing Hydroxyapatite Porous Particles and Silver-Containing Hydroxyapatite Sintered Particles>>

Figure 11:
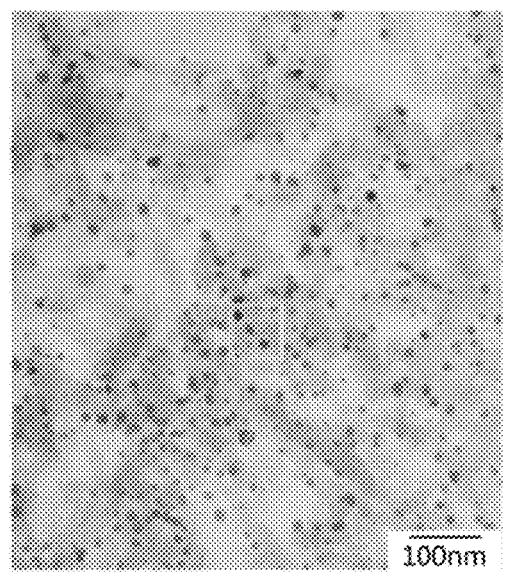
FIG. 11 is an image from a transmission electron microscope of a cross-section of the silver-containing hydroxyapatite porous particle (Example 5).

The silver-containing hydroxyapatite porous particles obtained in Example 5 were embedded in a resin and then a cross-section was smoothed by polishing. A ultrathin sections were selected by focused ion beam method and slices with a thickness of about 30 nm were prepared. Using the same, shapes of the silver particles were examined by the transmission electron microscope and scanning transmission electron microscope and energy dispersive X-ray analyzed was carried out. As shown in FIG. 11, silver particles of 1-20 nm were observed together with plate-like crystals of hydroxyapatite. The shape of the silver particles were nearly spherical, and needle-like particles or flattened particles were not observed.

<<Surface Analysis of Silver-Containing Hydroxyapatite Porous Particles and Silver-Containing Hydroxyapatite Sintered Particles>>

Figure 12:
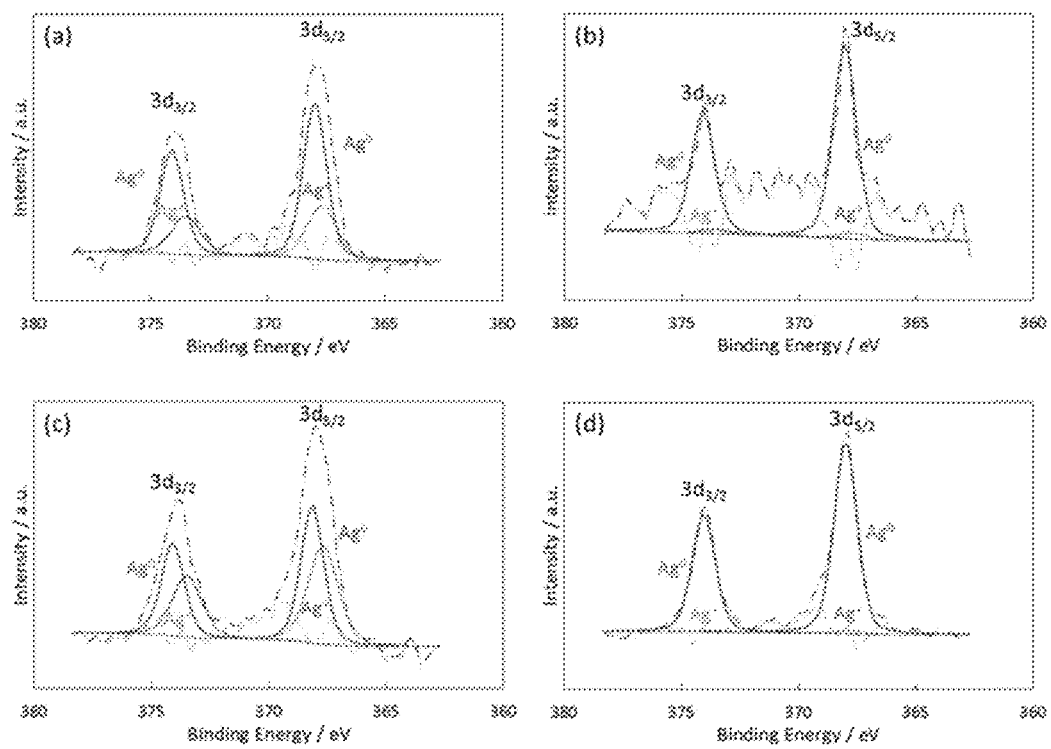
FIG. 12 are charts showing photoelectron spectroscopic spectra of the silver-containing hydroxyapatite porous particles (a: Example 5, c: Comparative Example 2) and the silver-containing hydroxyapatite sintered particles (b: Example 5, d: Comparative Example 2).

Surface characteristics of silver-containing hydroxyapatite porous particles and silver-containing hydroxyapatite sintered particles obtained by calcining them at 1200° C., for 30 minutes, which were prepared in Example 5 and Comparative Example 2, were analyzed by X-ray photoelectron spectroscopy. The results are shown in FIG. 12, respectively. The peaks located at 3/2 and 5/2 of the 3d orbit of Ag are separated into peaks attributable to $Ag^0$ (simple substance of silver) and Ag (silver bound to monovalent cation). The binding energies of $Ag^0$ and $Ag^+$ at $3d_{3/2}$ were observed at 374.1 eV and 373.5 eV, and the binding energies of $Ag^0$ and Ag at $3d_{5/2}$ were observed at 368.0 eV and 367.7 eV. In the silver-containing hydroxyapatite porous particles prepared in Example 5 and Comparative Example 2, the mass ratios of $Ag^+$ and $Ag^0$ were 33/67 and 53/47, respectively. It can be seen that many silvers precipitated by vapor deposition method. While, in the silver-containing hydroxyapatite sintered particles prepared in Example 5 and Comparative Example 2, mass ratio of $Ag^0$ was close to 100. Thus, it can be understood that $Ag^+$ was reduced by calcining and became simple substance of silver.

<<Composition Distribution within Silver-Containing Hydroxyapatite Porous Particle>>

Figure 13:
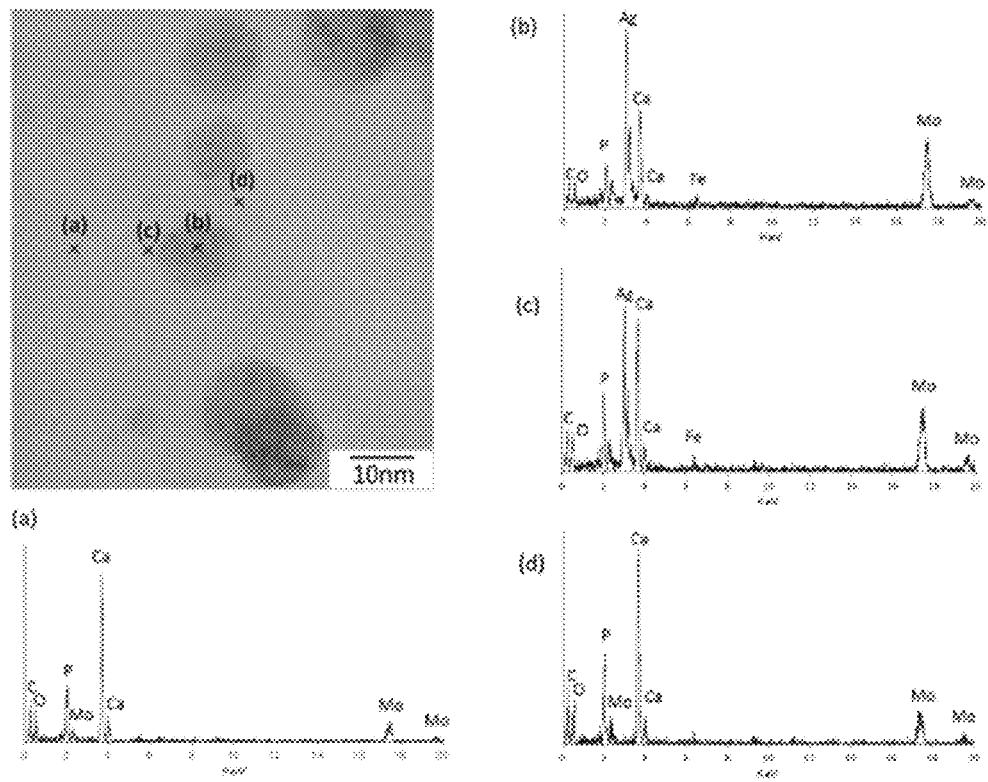
FIG. 13 is an image from a transmission electron microscope of a cross-section of the silver-containing hydroxyapatite porous particle (Example 5) and results of an energy dispersive X-ray analyses at each site.

FIG. 13 shows a transmission electron microscope image of the enlarged silver-containing hydroxyapatite porous particles, and the results of the elemental analysis of each part of a-d. In the transmission electron microscope image, silver particles of about 10 nm are observed as black particles, and the peripheries thereof are hydroxyapatite. At the site of "a", calcium and phosphorus were observed, and almost no silver was detected. At the site of "b", there were many silver and calcium and phosphorus were slightly detected. This is because hydroxyapatite is always present in the section since the thickness of the section is 30 nm. At the boundary between silver and hydroxyapatite in "c", silver, calcium and phosphorus were detected respectively. The site of "d" is a part where the lattice of hydroxyapatite could be recognized. In this part, calcium and phosphorus were detected, but almost no silver was detected. From this result, it is considered that silver is not substituted in the lattice of hydroxyapatite.

<<Size of Silver in Silver-Containing Hydroxyapatite Porous Particle>>

Figure 14:
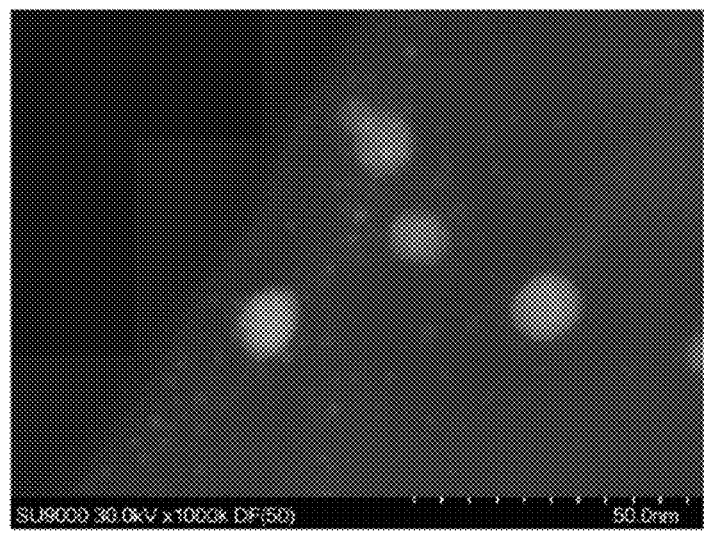
FIG. 14 is an image from a scanning transmission electron microscope of a cross-section of the silver-containing hydroxyapatite porous particle (Example 5).

FIG. 14 shows the observation of the silver-containing hydroxyapatite porous particles by scanning transmission electron microscope. A heavy element appears white. From these results, it was found that the silver particles prepared by the method of Example 5 contained small silver particles of 1 nm to 5 nm together with silver particles having a diameter of about 20 nm.

<<Localization of Silver Particles in Silver-Containing Hydroxyapatite Sintered Particle>>

The localization of the silver particles in silver-containing hydroxyapatite sintered particles obtained in Example 5 was examined using image processing/image analysis software (winROOF, Mitani Corporation). The cross-section of the silver-containing hydroxyapatite sintered particles was regarded as a circle, and the particle diameter of the silver particles contained therein was measured. The particle size distribution of the silver particles (circle equivalent diameter: diameter of a circle having the same area as the projected area of the particle) was 0.08 to 0.38 pin, and the average particle diameter was 0.22 μm.

Figure 15:
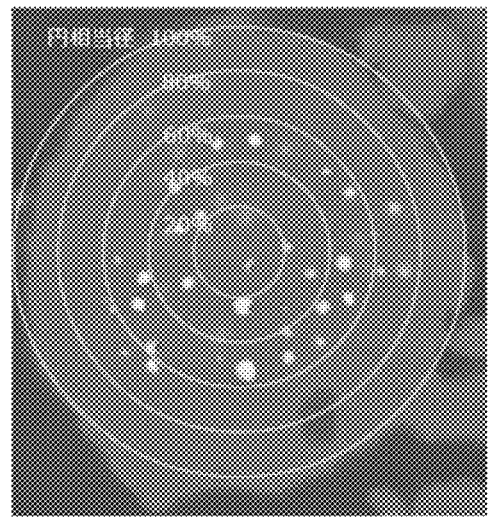
FIG. 15 is a photograph showing a localization of silver particles in the silver-containing hydroxyapatite sintered particle, and a histogram. The photograph (a) shows the localization of silver particles within the radii 20, 40%, 60%0, 80% and 100% when the silver-containing hydroxyapatite sintered particle is regarded as a circle. The histogram (b) shows the area of silver particles in each section.
Figure 15:
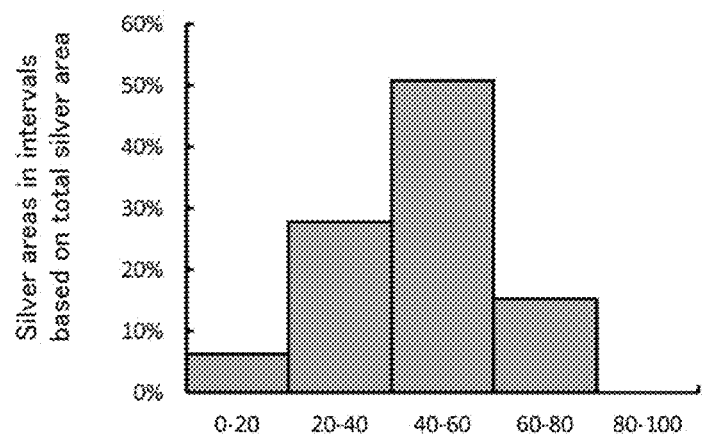

The number and the area of the silver particles contained in the circle centered on the gravity center of the silver-containing hydroxyapatite sintered particles were measured. The silver particles were not present on the surface layer of the silver-containing hydroxyapatite sintered particles, and all silver particles were present in the range of 80% of the circle equivalent diameter (FIG. 15 and Table 1).

TABLE 1

| Diameter of circle (Ratio to circle equivalent diameter) | Number of silver particles | Area of silver ($\mu m^2$) |
|---|---|---|
| 20% | 2 | 0.116 |
| 40% | 15 | 0.638 |
| 60% | 36 | 1.587 |
| 80% | 43 | 1.872 |
| 100% | 43 | 1.872 |

<<Measurement of Silver Content>>

Silver content of the resulting silver-containing hydroxyapatite sintered particle was measured by ICP emission spectrometry after completely dissolving 1 mg of the sample in 0.1 mol/L of nitric acid aqueous solution (10 mL). The silver contents of each particle are shown below.

TABLE 2

|  | Hydroxyapatite porous particle | Calcination temperature | Silver content (% by weight) |
|---|---|---|---|
| Example 2 | HAp-60 | 1200° C. | 0.70 |
| Example 5 | HAp-60 | 1200° C. | 6.38 |

<<Silver Elution Test: Short Term>>

The elution of silver from the obtained silver-containing hydroxyapatite sintered particles for a short term was examined.

Figure 16:
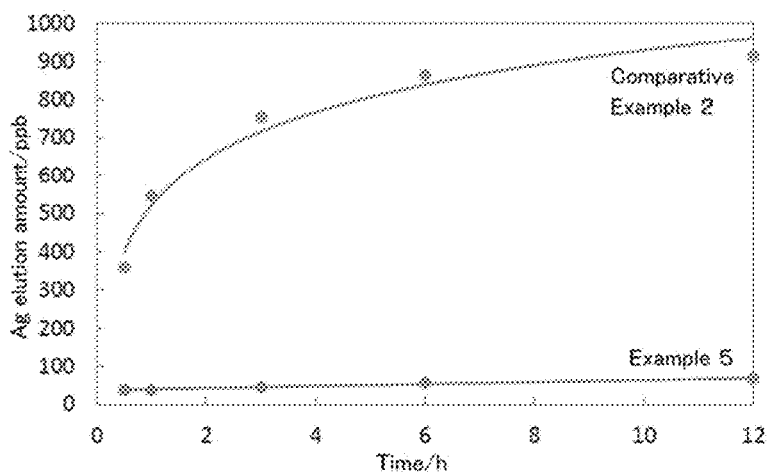
FIG. 16 is a graph showing results of silver elution tests of the silver-containing hydroxyapatite sintered particles obtained in Example 5 and Comparative Example 2.

A sample (20 mg) was placed in 10 mL of Dulbecco's phosphate buffer solution (D-PBS, pH 7.3) and the whole was inverse at 37° C. After a predetermined time, solids were separated from liquid by centrifugation, and 2 mL of the supernatant was extracted. Then, 3 mL of ultrapure water was added thereto, and it was subjected to ICP mass spectrometry. Further, 2 mL of D-PBS was added to the sample after extraction and the sample was continuously tested. Particles prepared in Example 5 and Comparative Example 2 (particles calcined at 1200° C.) were used. The time course of eluted silver is shown in FIG. 16. In the sample of Comparative Example 2 in which simple substance of silver was precipitated on the particle surface, the elution amount after 12 hours was 13 times, and silver ion was eluted at the early stage. Whereas, in the sample of example 5, the elution amount of silver was extremely low. The reason for this difference is considered to be that in Comparative Example 2, simple substance of silver was formed on the particle surface.

<<Silver Elution Test: Intermediate Term>>

The elution of silver from the obtained silver-containing hydroxyapatite sintered particles for an intermediate term was examined.

Figure 17:
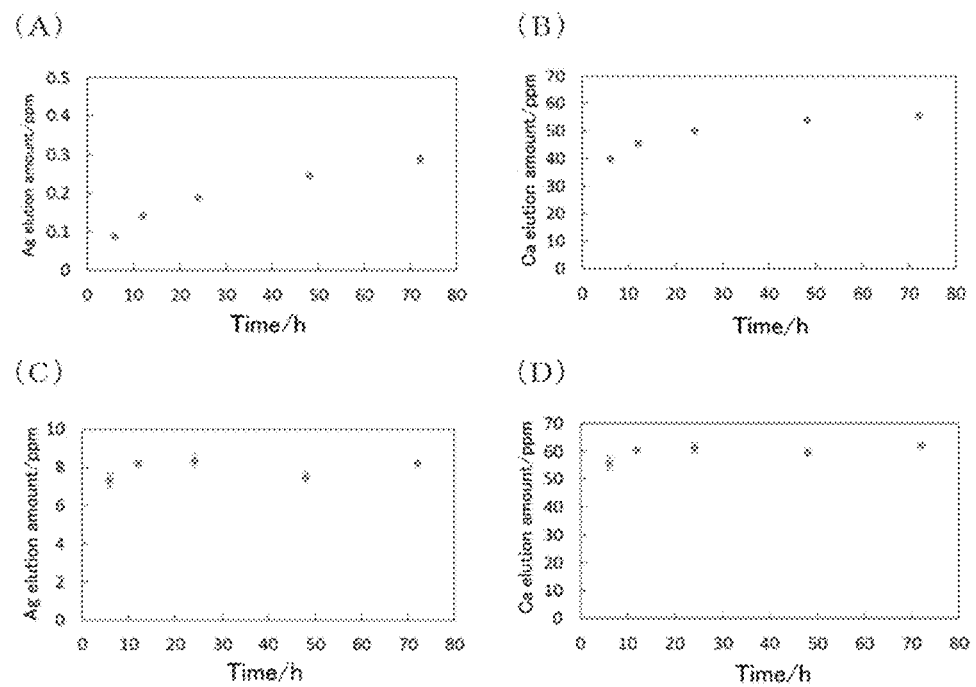
FIG. 17 is a graph showing results of elution tests of silver ion (A) and calcium ion (B) of silver-containing hydroxyapatite sintered particles obtained in Example 5, and silver ion (C) and calcium ion (D) of silver-containing hydroxyapatite sintered particles obtained in Comparative Example 2.

A sample (5 mg) was placed in 10 mL of acetic acid-sodium acetate buffer solution (pH5.5, 0.8 mol/L) and the whole was inversed at 37° C. After a predetermined time, solids were separated from liquid by centrifugation, and a total volume was extracted. Then, silver and calcium were analyzed by ICP mass spectrometry. The particles calcined at 1200° C. obtained in Example 5 and Comparative Example 2 were used. The time courses of eluted silvers are shown in FIG. 17. The elution behaviors of calcium ions were almost the same for both samples. On the other hand, the elution amount of silver ions after 3 days was 0.3 ppm in the sample of Example 5, but was 8 ppm in the sample of Comparative Example 2. That is, the elution amount of the sample of Example 5 was 27 times or less of that of Comparative Example 2, and was extremely low. The reason for this difference is considered to be that in Comparative Example 2, simple substance of silver was formed on the particle surface.

Example 6

In this Example, formaldehyde was applied to hydroxyapatite porous particles by the vapor deposition method to prepare silver-containing hydroxyapatite porous particles, and silver-containing calcium phosphate sintered particles.

2.5 mL of formaldehyde aqueous solution (10% by weight) was placed at a bottom of a vacuum desiccator and 0.5 g of HAp-60, HAp-400, HAp-600, or HAp-800 was placed therein, and then, the vacuum desiccator was depressurized and allowed to stand at 37° C. for 24 hours. Subsequently, 0.787 g of silver nitrate was added to a solution obtained by adding 25% aqueous ammonia (0.9 mL) to ultrapure water (25 mL), and the formaldehyde-applied, hydroxyapatite porous particles were added thereto. The whole was stirred for 3 hours at room temperature. Under the same conditions as above, the solid phase was separated by centrifugation and washed twice with ultrapure water to obtain hydroxyapatite porous particles in which silver particles were precipitated. They were vacuum-dried at 60° C., and calcined at 1200° C. for 30 minutes to obtain the silver-containing calcium phosphate sintered particles.

<<Measurement of Silver Content>>

Figure 18:
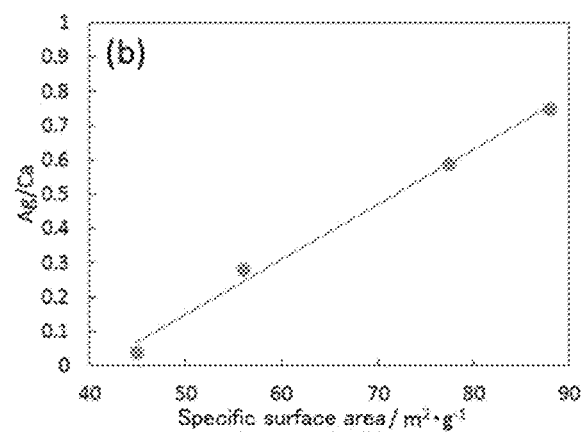
FIG. 18 is a graph showing the relationship between an amount of silver that can be supported on silver-containing hydroxyapatite sintered particles (Ag/Ca amount ratio) and specific surface area of the hydroxyapatite porous particles.

Silver contents of the resulting silver-containing hydroxyapatite porous particles and the silver-containing hydroxyapatite sintered particle were measured by ICP emission spectrometry after completely dissolving 1 mg of each sample in 0.1 mol/L of nitric acid aqueous solution (10 mL). The silver contents of each particle are shown in Table 2 and FIG. 18. It was found that as the specific surface area of the hydroxyapatite porous particle decreased, the amount of silver supported on the silver-containing hydroxyapatite sintered particle also decreased, as shown in FIG. 18.

TABLE 3

| Hydroxyapatite porous particle | Calcination temperature | Silver content (% by weight) | Ag/Ca (Ratio by weight) |
|---|---|---|---|
| HAp-60 | Not calcined | 24.1 | 0.88 |
|  | 1200° C. | 19.3 | 0.75 |
| HAp-400 | Not calcined | 23.5 | 0.85 |
|  | 1200° C. | 18.5 | 0.59 |
| HAp-600 | Not calcined | 15.3 | 0.48 |
|  | 1200° C. | 8.61 | 0.28 |
| HAp-800 | Not calcined | 5.11 | 0.14 |
|  | 1200° C. | 1.41 | 0.04 |

Example 7

In this example, hydroxyapatite porous particles in which silver particles were precipitated (silver-containing hydroxyapatite porous particles) were formed and the resulting molded body was calcined to prepare the silver-containing calcium phosphate sintered compact (silver-containing calcium phosphate sintered body).

The hydroxyapatite porous particles (0.19 g) in which silver particles were precipitated, prepared using HAp-60 in Example 5, were filled in a metallic mold and subjected to uniaxial pressure of 20 MPa for 1 minute to prepare a molded body. The temperature was raised at 600° C./hour and the molded body was kept at 1200° C. for 30 minutes to prepare a sintered body, which was referred to as sample A. The density of the sample A was 2.80 g/cm³. The silver contained in sample A was 10.56% by weight.

Comparative Example 6

The procedure of Example 7 was repeated to prepare a sintered body, except that the hydroxyapatite porous particles in which silver particles were precipitated (silver-containing hydroxyapatite porous particles) prepared in Comparative Example 2 was used, instead of the hydroxyapatite porous particles in which silver particles were precipitated (silver-containing hydroxyapatite porous particles) prepared in Example 5. It was referred to as sample B. The density of the sample B was 2.24 g/cm³. The silver contained in sample B was 9.20% by weight.

Figure 19:
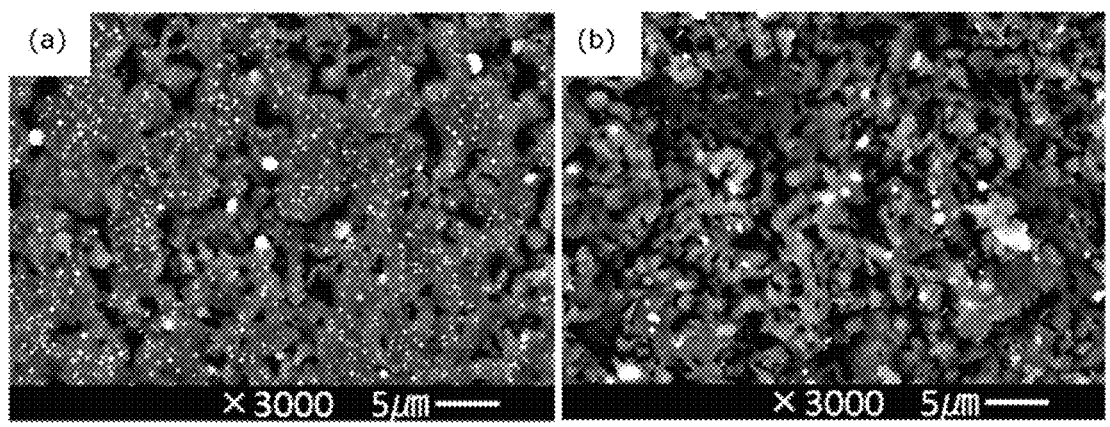
FIG. 19 is an image from a backscattered electron microscope of fracture cross-sections of the silver-containing calcium phosphate sintered compact prepared by using the hydroxyapatite porous particles to which formaldehyde is applied by vapor deposition method (a) (Example 7), and the silver-containing calcium phosphate sintered compact prepared by using the hydroxyapatite porous particles to which silver is bound by using the silver nitrate aqueous solution (b) (Comparative Example 6).

The backscattered electron microscopic images of fracture cross sections obtained by breaking the sample A and sample B were shown in FIGS. 19a and 19b, respectively. As shown in FIG. 19a, it was found that the silver nanoparticles are uniformly distributed in the sample A. Further, comparing the sizes of the silver nanoparticles in each sample, the particles contained in sample A were clearly small and the large silver nanoparticles were formed in sample B in FIG. 19b. A backscattered electron microscopic image of the fracture surface of Sample A observed at high magnification is shown in FIG. 20. Hydroxyapatite grains having a size of about 0.5 μm were observed, and it could be seen that silver was distributed in the grain boundary composed of three grains. Even when seeing the whole image, silvers were present in the grain boundaries.

<<Silver Elution Test>>

Figure 21:
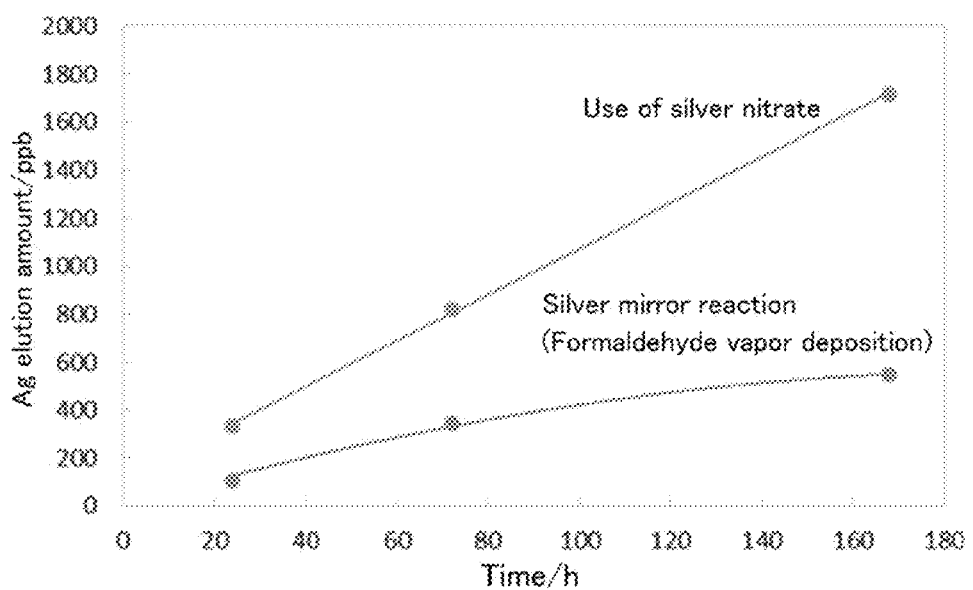
FIG. 21 is a graph showing results of silver elution tests of the silver-containing calcium phosphate sintered compact obtained in Example 7 and the silver-containing calcium phosphate sintered compact obtained in Comparative Example 6.

The sample A (φ6.69 mm×1.79 mm, 0.175 g) of Example 7 and sample B (φ7.3 mm×1.87 mm, 0.178 g) were immersed in 5 mL of D-PBS, and solutions were collected, and then they were subjected to ICP mass spectrometry. The total amount of the supernatant of D-PBS was collected and tests were continuously carried out by newly adding D-PBS to the samples. The elution curves of silver are shown in FIG. 21. As shown in the figure, the elution amount of silver from sample A was significantly lower than the elution amount of silver of sample B, and it is suppressed to ⅓ after 1 week.

<<Area Ratio>>

Figure 22:
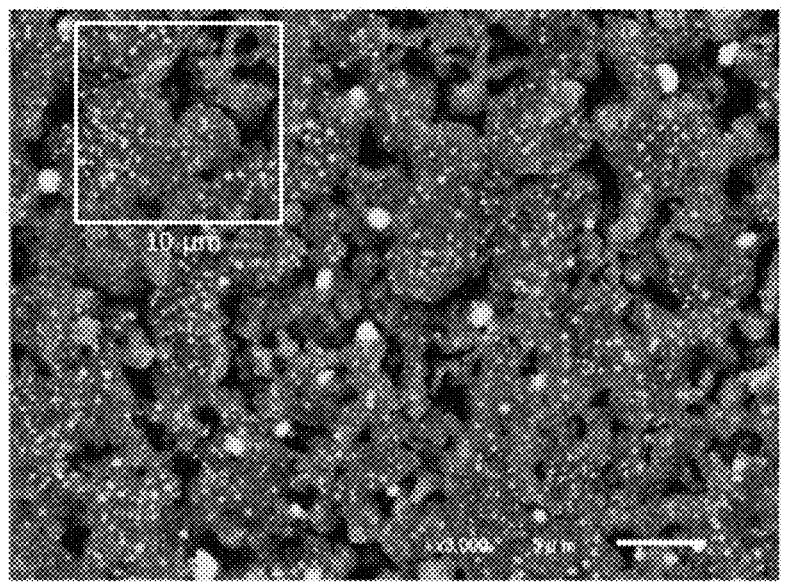
FIG. 22 is photograph showing an example of a measurement area for determining area ratio of the silver particles in the cross-section of the silver-containing calcium phosphate sintered compact.

The area ratio of silver particles in a 10 μm square (100 μm$^2$) randomly selected in the cross sections of the sample A of Example 7 and the sample B of Comparative Example 6 was measured. Ten points were measured and the average was calculated. An example of the measurement area of the sample A is shown in FIG. 22 and the results are shown in Table 4. The area ratio of the sample A was 3.4% and the area ratio of the sample B was 1.7%. The parentheses indicate the maximum and minimum area ratios in the measured squares.

TABLE 4

|  | Area ratio |
| --- | --- |
| Example 6 | 3.4 |
|  | (1.9-5.5) |
| Comparative Example 6 | 1.7 |
|  | (0.3-5.5) |

<<Number of Silver Particles>>

The number of silver particles in the cross-section (12.6 μm$^2$) of a particle with a diameter of 4 μm in Example 5 were measured, and the number of silver particles in ten positions of 10 μm square (100 μm$^2$) randomly selected in the cross-sections of the sample A of Example 7 and the sample B of Comparative Example 6 were measured. The results are shown in Table 5.

TABLE 5

|  | Measured area | Number of silver particles |
| --- | --- | --- |
| Example 5 | 100 μm$^{2(*1)}$ | 48-215 |
| Example 7 | 100 μm$^2$ | 43-116 |
| Comparative Example 6 | 100 μm$^2$ | 0-13 |

(*1)The cross sectional area of 100 μm$^2$ was measured by summing the cross sectional areas of particles of 12.6 μm$^2$.

Example 8

The procedure of Example 5 was repeated to prepare the hydroxyapatite porous particles in which silver particles were precipitated, except for changing the amount of solution, the amount of hydroxyapatite porous particles, and the like. Then, the silver-containing calcium phosphate sintered particles were prepared by calcining them using each of calcination methods.

Specifically, 10 mL of formaldehyde aqueous solution (10%) was placed at a bottom of a vacuum desiccator and 10.0 g of HAp-60 was placed therein, and then, the vacuum desiccator was depressurized and allowed to stand at 37° C. for 24 hours. Subsequently, 1.75 g of silver nitrate was added to a solution obtained by adding 25% aqueous ammonia (2.0 mL) to ultrapure water (500 mL), and the whole was stirred for 3 hours. Under the same conditions as above, the solid phase was separated by centrifugation and washed twice with ultrapure water. They are vacuum-dried at 60° C.

<<Preparation of Sintered Compact by Cold Isostatic Pressing Method>>

Figure 23:
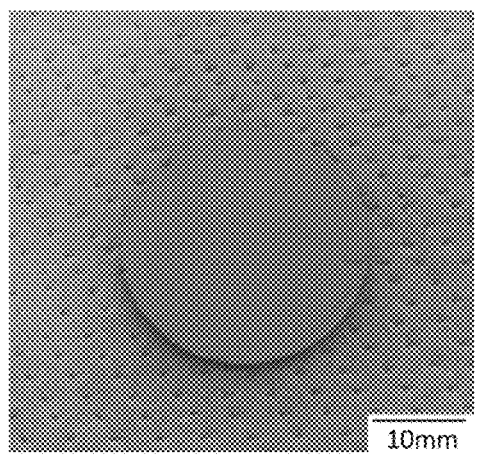
FIG. 23 is an exterior photograph of the silver-containing hydroxyapatite sintered compact prepared by a cold isostatic pressing method.

The resulting silver-containing hydroxyapatite porous particles (4.5 g) were filled in a metallic mold (φ44 mm) and subjected to uniaxial pressure of 10 MPa for 3 minutes to prepare a molded body. The molded body was placed in rubber and sealed. 1.2 tons of pressure was applied thereto by cold isostatic pressing (CIP), and kept for 5 minutes. After removing the load, it was taken out. The temperature was raised at 600° C./hour and the molded body was kept at 1200° C. for 3 hours. It was referred to as sample C. The density of the sample C was 3.17 g/cm$^3$. The silver contained in sample C was 11.5% by weight. The appearance of the resulting silver-containing hydroxyapatite sintered compact is shown in FIG. 23.

Example 9: Preparation of Sintered Compact by Hot Pressing Method

Figure 24:
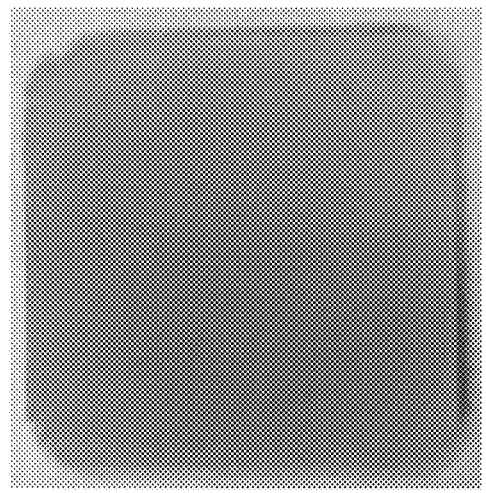
FIG. 24 is an exterior photograph of the silver-containing hydroxyapatite sintered compact prepared by a hot pressing method.

The silver-containing hydroxyapatite porous particles (8.0 g) prepared in Example 8 were filled in a carbon mold (35×35 mm). While raising the temperature at 1800° C./hour under a vacuum atmosphere, it was subjected to uniaxial pressure of 30 MPa up to 200° C., and the pressure was maintained. It was kept at 1200° C. for 30 minutes, and cooled to room temperature after removing the load (hot press method; HP). It was referred to as sample D. The density of the sample D was 3.33 g/cm$^3$. The silver contained in sample D was 12.2% by weight. The appearance of the resulting sintered compact is shown in FIG. 24.

Example 10: Preparation of Sintered Compact by Spark Plasma Sintering Method

Figure 25:
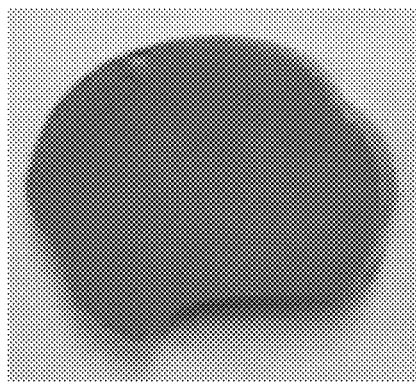
FIG. 25 is an exterior photograph of the silver-containing hydroxyapatite sintered compact prepared by a spark plasma sintering method.

The silver-containing hydroxyapatite porous particles (0.7 g) prepared in Example 8 were filled in a carbon mold (φ10 mm), and subjected to uniaxial pressure of 30 MPa. The temperature was raised rapidly to 600° C. while maintaining the pressure. Then, the temperature was raised to 1200° C. in 12 minutes and kept for 10 minutes (spark plasma sintering method; SPS). It was referred to as sample E. The density of the sample E was 3.08 g/cm$^3$. The silver contained in sample D was 11.0% by weight. The appearance of the resulting sintered compact is shown in FIG. 25.

<<Morphology and Size of Silver in Each Sintered Compact>>

Figure 26:
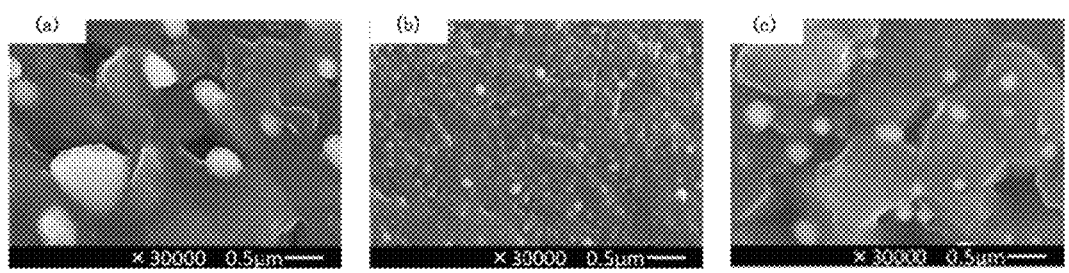
FIG. 26 are images from scanning electron microscope showing silver particles distribution in cross-section of silver-containing hydroxyapatite sintered compacts prepared by a cold isostatic pressing method (a), a hot pressing method (b), and a spark plasma sintering method (c).

The backscattered electron microscopic images of each of fracture cross sections obtained by breaking the sample C, sample D, and sample E were shown in FIG. 26. In the cross section of the sample C, silver nanoparticles with an average particle diameter of 0.38±0.11 μm were uniformly observed at the grain boundary. In the cross section of the sample D, silver nanoparticles with an average particle diameter of 0.10±0.02 μm were uniformly observed at the grain boundary. Further, in the cross section of the sample E, silver nanoparticles with an average particle diameter of 0.20±0.10 μm were uniformly observed at the grain boundary. The size of silver nanoparticles became smaller by raising the temperature while pressurizing, as above.

<<Method for Removing Contaminated Carbon>>

Figure 27:
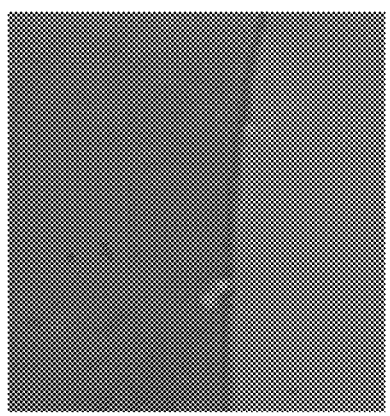
FIG. 27 is an appearance of the sample in which the silver-containing hydroxyapatite sintered compact prepared by the hot press method, is heat-treated again to burn contaminated carbon. The left is before heat treatment and the right is after heat treatment.
Figure 28:
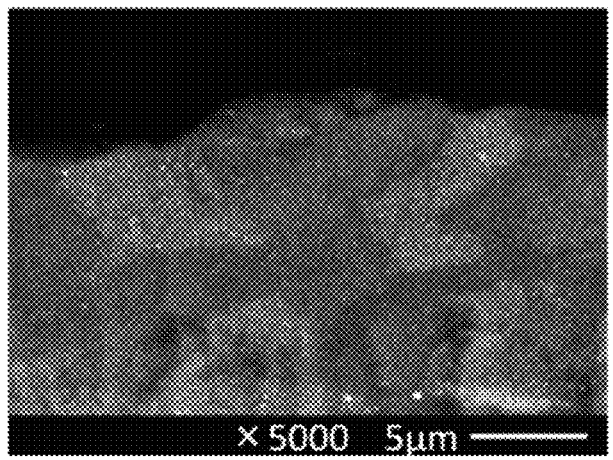
FIG. 28 is an image from scanning electron microscope showing a cross-section of the silver-containing hydroxyapatite sintered body prepared by the hot press method, which is heat-treated for carbon desorption.

When the carbon mold was used, carbon is contaminated in the surface and inside thereof, and thus the resulting sintered compact were heat-treated again and excess carbons were removed. The sample D was broken, and the temperature was raised at a rate of 10° C./min (up to 800° C.) and kept for 30 minutes. The color difference of the resulting sample is shown in FIG. 27. As shown in the figure, the untreated sample (left side) had blackness, while the sample after heating treatment (right side) turned bright yellow. Further, from the results of powder X-ray diffraction measurement, no evaporation of silver was observed. Furthermore, from the backscattered electron image of the scanning electron microscope shown in FIG. 28, it was found that silver was not desorbed from the surface of the sintered compact by the heat treatment at 800° C.

<<Silver Elution Test of Sintered Compact>>

The silver elution from the sintered compact calcined at 1200° C., which was prepared in Example 9, i.e. sample D, was examined.

Figure 29:
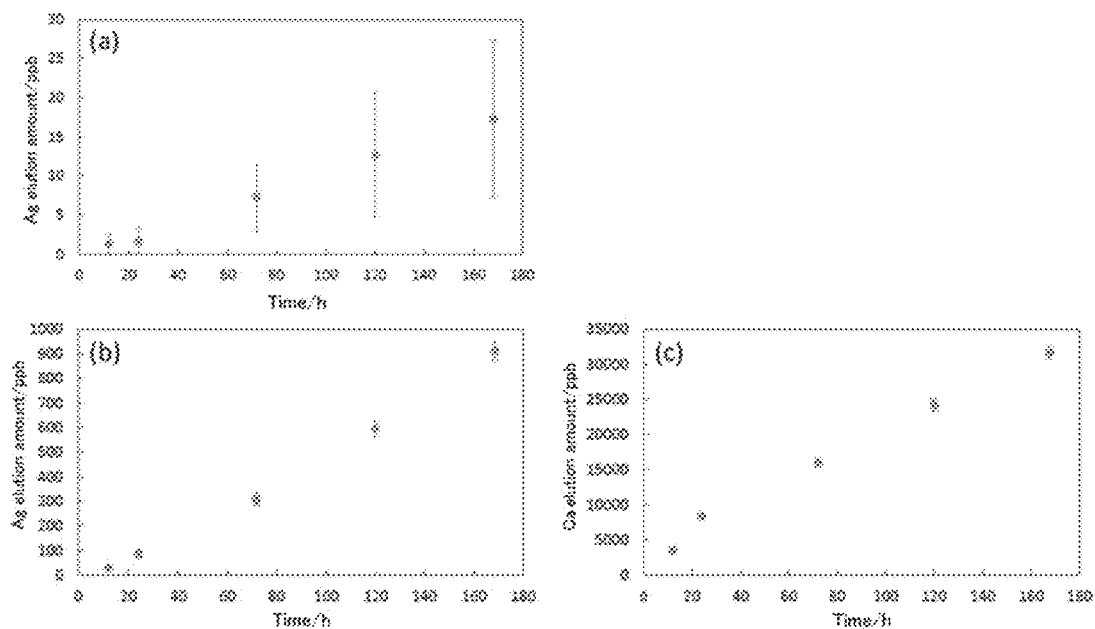
FIG. 29 are graphs showing results of silver elution test of the prepared sintered body (sample D). The silver ion elution in Dulbecco's phosphate buffer solution (D-PBS) is shown in (a), and the silver ion elution and calcium ion elution in acetic acid-sodium acetate buffer are shown in (b) and (c) respectively.

A sample (120 mg) in which the Sample D was cut to about 5 mm$^2$ with a diamond cutter, was placed in 10 mL of D-PBS or acetic acid-sodium acetate buffer solution (pH5.5, 0.8 mol/L), and allowed to stand at 37° C. After a predetermined time, 8 mL of the solution was extracted, and silver and calcium were analyzed by ICP mass spectrometry. Further, 8 mL of the same buffer solutions were added thereto after extraction and the sample was continuously tested. The time courses of eluted silvers are shown in FIG. 29. In the case of D-PBS, the elution amount of calcium ion was less than the detection limit. The elution amount of silver ion until 24 hours was extremely low (i.e. about 2 ppb) but it became 15 ppb after 7 days. Compared with the results of the silver elution test of Sample A (sintered compact prepared in Example 7) conducted in Comparative Example 6, when converting the test piece to the same weight and taking the solution amount into account, it was found that the elution amount was suppressed to about 1/10. On the other hand, in the case of acetate-sodium acetate buffer solution, the elution amount of calcium ion linearly increased and was about 30 ppm after 7 days. Further, the elution amount of silver ion also increased linearly and was about 900 ppb after 7 days.

Example 11: Preparation of Sintered Compact Controlling Silver Particles Distribution The silver-containing hydroxyapatite porous particles prepared in Example 8 and hydroxyapatite porous particles were mixed so that the silver content was 1% by weight, and a silver-containing hydroxyapatite sintered compact was prepared under the same conditions of the method (hot pressing method) in Example 9. It was referred to as sample F-1. Further, the silver-containing hydroxyapatite porous particles were prepared under the same conditions as the method in Example 8, except that the amount of silver nitrate was 0.175 g which was 1/10 of that in Example 8, and the silver-containing hydroxyapatite sintered compact was prepared under the conditions of the method (hot pressing method) in Example 9. It was referred to as sample F-2.

<<Silver Elution Test of Sintered Compact>>

The silver elution from the silver-containing hydroxyapatite sintered compacts prepared so as to have the same silver content, i.e. sample F-1 and sample F-2, were examined.

Figure 30:
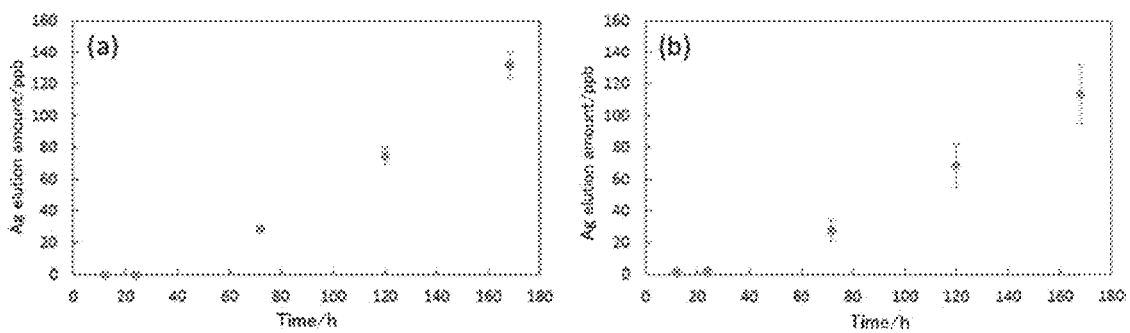
FIG. 30 are graphs showing results of silver elution tests of sample F-1 (a) and sample F-2 (b) which are sintered bodies with different distribution of silver.

120 mg of Sample F-1 and sample F-2 cut with a diamond cutter into about 5 mm$^2$ were placed in 10 mL of D-PBS, and allowed to stand at 37° C. After a predetermined time, 8 mL of solution was extracted, and silver was analyzed by ICP mass spectrometry. After 12 hours, 1 day, 3 days, 5 days, and 7 days, each of the elution amounts of silver ion were less than the detection limit by ICP analysis. On the other hand, 120 mg of Sample F-1 and sample F-2 cut with a diamond cutter into about 5 mm$^2$ were placed in 10 mL of acetic acid-sodium acetate buffer solution (pH5.5, 0.08 mol/L), and allowed to stand at 37° C. After a predetermined time, 8 mL of solution was extracted, and silver was analyzed by ICP mass spectrometry. Further, 2 mL of the same buffer solution was added to the sample after extraction and the sample was continuously tested. The time courses of eluted silvers are shown in FIG. 30. The elution amount of silver ions until 24 hours was less than the detection limit by ICP analysis, but became about 110 ppb after 7 days. Thus, elution of silver ions was not detected in the neutral buffer solution, and elution of silver ions occurred only in a buffer solution of pH5.5, which mimicked inflammation.

Example 12

*Escherichia coli* was inoculated into the silver-containing hydroxyapatite sintered compact (sample C) prepared by the cold isostatic pressing method in Example 8, and a silver-free hydroxyapatite sintered compact (comparative sample) prepared by the cold isostatic pressing method, and an antimicrobial test was carried out after 24 hours. The procedure of Example 8 was repeated to prepare the comparative sample, except that silver-free hydroxyapatite porous particles were used.

Specifically, a liquid containing *Escherichia coli* (2.5×10$^5$-1.0×10$^6$ cells/mL) was placed dropwise on the sintered compact, and covered with a polyethylene film. Then, it was cultured for 24 hours under the conditions of 35° C. and a relative humidity 90% or more. Subsequently, the culture sample was washed with 10 mL of "soybean casein digest brith with lecithin and polysorbate 80" (SCDLP) medium, and the medium was serially diluted by a factor of 10. The resulting dilutions were inoculated on SCDLP agar medium and incubated for 48 hours at 35° C. Then, the number of viable cells was calculated from the number of formed colonies. As shown in Table 6, the viable cell number on the sample C at 24 hours after inoculation was less than 1/20 of that of the comparative sample. From the above results, it is understood that Sample C has an antibacterial effect.

TABLE 6

| Sample | Initial number of bacteria (cells/mL) | Number of viable bacterias after 24 hours (cells/plate) |
|---|---|---|
| Comparative sample | 2.5 × 10$^5$ | 2.3 × 10$^2$ |
| Sample C | 2.5 × 10$^5$ | <10$^1$ |

Example 13

10 g of the silver-containing hydroxyapatite sintered particle prepared in Example 5 was added to a mixed solution of 12 mL of ultrapure water and 1.2 g of polyethylenimine (crosslinking polymerization agent), and 0.6 mL of polyoxyethylene lauryl ether was added thereto as a foaming agent. The mixture was foamed by a propeller stirrer, and finally, for curing, predetermined amounts of an epoxy resin and curing agent were added. The mixture was placed in a mold having a φ11 mm and dried at 60° C. to prepare a molded body F.

<<Method for Calcining Porous Body>>

Figure 31:
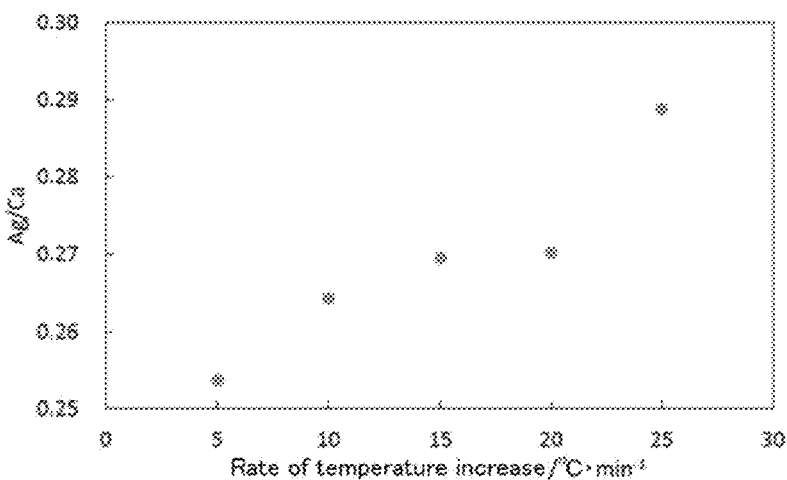
FIG. 31 is a graph showing a relationship between a rate of temperature increase and an Ag/Ca mass ratio, in the preparation of silver-containing hydroxyapatite sintered compact from silver-containing hydroxyapatite porous particles.

The molded body F was held in the atmosphere at a rate of 10° C./min (up to 300° C.), at a rate of 3.3° C./min (from 300° C. to 500° C.), and at 500° C. for 30 minutes. Further, the temperature was increased from 500° C. to 1200° C. at a rate of 5° C./min, 10° C./min, 15° C./min, 20° C./min, or 25° C./min, and kept for 3 hours. The porous body prepared under each condition was referred to as samples G, H, I, J, or K, respectively. The porosity thereof was 45.1%, 36.0%, 36.7%, 39.0%, or 32.9%, respectively. The silver contained in these samples was 9.96% by weight, 10.63% by weight, 10.76% by weight, 10.75% by weight, or 12.13% by weight, respectively. The relationship between the heating rate and the Ag/Ca mass ratio is shown in FIG. 31. That is, it can be seen that the evaporation amount of silver could be suppressed according to the calcination condition.

<<Distribution of Silver>>

Figure 32:
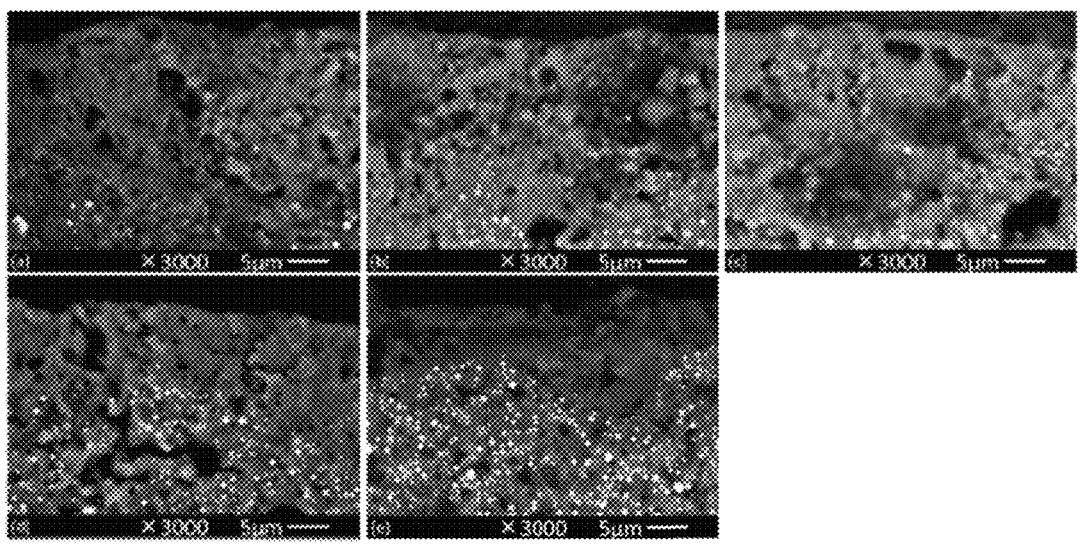
FIG. 32 are photographs by a scanning electron microscope, showing distribution of silver in the cross-section of the prepared porous bodies. (a): sample G, (b): sample H, (c): sample I, (d): sample J, (e): sample K.

The backscattered electron images of cross sections obtained by breaking the samples G, H, I, J, and K were shown in FIG. 32. The desorption of silver from the surface was different in depth depending on the site, but it could be seen that silver of about 20 μm, 19 μm, 16 μm, 11 μm, or 9 μm from the surface was evaporated, respectively. It was found that the evaporation amount of silver could be controlled according to the calcination condition.

Example 14

In this Example, formaldehyde was applied to hydroxyapatite porous particles, i.e. HAp-400, HAp-600, HAp-800, or HAp-1000, by the vapor deposition method to prepare silver-containing hydroxyapatite porous particles.

5 mL of formaldehyde aqueous solution (10% by weight) was placed at a bottom of a vacuum desiccator and 1 g of each hydroxyapatite porous particles was placed therein separately, and then, the vacuum desiccator was depressurized and allowed to stand at 37° C. for 24 hours. Subsequently, 0.118 g, 0.0554 g, or 0.0277 g of silver nitrate was added to a solution obtained by adding 25% aqueous ammonia (0.2 mL) to ultrapure water (25 mL), and the formaldehyde-applied, hydroxyapatite porous particles were added thereto, separately. The whole was stirred for 3 hours at room temperature. Under the same conditions as above, the solid phase was separated by centrifugation and washed twice with ultrapure water to obtain hydroxyapatite porous particles in which silver particles were precipitated (silver-containing hydroxyapatite porous particles). They are vacuum-dried at 60° C.

<<Measurement of Silver Content>>

Silver content of the resulting silver-containing hydroxyapatite porous particles was measured by ICP emission spectrometry after completely dissolving 1 mg of the sample in 0.1 mol/L of nitric acid aqueous solution (10 mL). The silver contents of each particle and abbreviated names are shown in FIG. 7.

TABLE 7

| Hydroxyapatite porous particle | Silver contents (% by weight) | abbreviated name |
|---|---|---|
| HAp-400 | 0.43 | Ag5_HAp-400 |
|  | 0.24 | Ag25_HAp-400 |
|  | 0.12 | Ag125_HAp-400 |
| HAp-600 | 0.49 | Ag5_HAp-600 |
|  | 0.20 | Ag25_HAp-600 |
|  | 0.10 | Ag125_HAp-600 |
| HAp-800 | 0.43 | Ag5_HAp-800 |
|  | 0.24 | Ag25_HAp-800 |
|  | 0.08 | Ag125_HAp-800 |
| HAp-1000 | 0.13 | Ag5_HAp-1000 |
|  | 0.03 | Ag25_HAp-1000 |
|  | 0.04 | Ag125_HAp-1000 |

<<Measurement of Surface-Enhanced Raman Scattering of Folic Acid Using Silver-Containing Hydroxyapatite Porous Particles>>

Surface-enhanced Raman scattering of folic acid in a certain concentration of folic acid aqueous solution was measured using the Ag5_HAp-800, Ag25_HAp-800, and Ag125_HAp-800, and the optimum silver-containing amount was examined.

Figure 33:
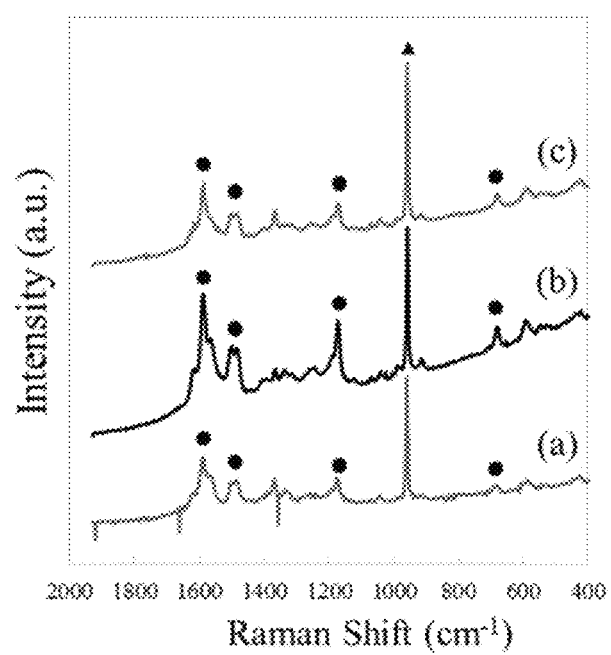
FIG. 33 is a chart showing the surface-enhanced Raman spectra measured by immersing the silver-containing hydroxyapatite particles (The particles are prepared using the hydroxyapatite porous particles preliminary-calcined at 800° C. (a): Ag5_HAp-800, (b): Ag25_HAp-800, (c): Ag125_HAp-800) having different silver-supporting amounts in a folic acid aqueous solution of $1 \times 10^{-6}$ mol/L.

Each silver-containing hydroxyapatite particle was added to a sodium chloride aqueous solution (0.06 mol/L) wherein folic acid concentration was adjusted to $1 \times 10^{-6}$ mol/L, and Raman spectroscopic analysis was performed with a laser light source with a wavelength of 532.18 nm. The measured Raman spectra are shown in FIG. 33. Raman lines attributed to folic acid were detected at 1621 $cm^{-1}$, 1589 $cm^{-1}$, 1564 $cm^{-1}$, and 1174 $cm^{-1}$, and Raman lines attributed to hydroxyapatite were detected at around 1366 $cm^{-1}$, and 957 $cm^{-1}$. The intensity of the Raman line attributed to folic acid (after subtracting the background) was calculated by considering the intensity of the Raman line attributed to the phosphoric acid of hydroxyapatite at 957 $cm^{-1}$ as 100. As a result, it was found that hydroxyapatite particles containing 0.24% by weight of silver, which has a small silver content, exhibited about twice the detection sensitivity of folic acid.

TABLE 8

| | Raman shift ($cm^{-1}$) | Attribution |
|---|---|---|
| Folic acid | 1621 | Deformation vibration of $NH_2$ or $H_2O$ (scissoring) |
|  | 1589 | C=C stretching (benzene ring) |
|  | 1564 | C=N stretching (pteridine ring) |
|  | 1174 | CH + $CH_2$ + NH wagging vibration |
| Hydroxyapatite | 1362 | $CO_3^{2-}$ impurities |
|  | 966 | Phosphate group |

<<Measurement of Surface-Enhanced Raman Scattering of Folic Acid with Different Concentrations>>

Surface-enhanced Raman scattering of folic acid in folic acid aqueous solutions with different concentrations was measured using the Ag25_HAp-800.

Figure 34:
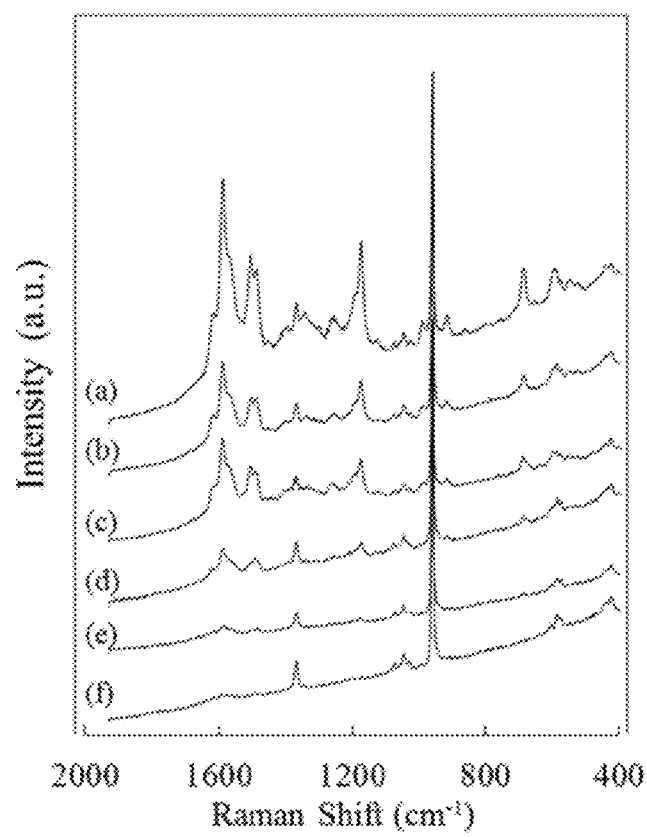
FIG. 34 is a chart showing the surface-enhanced Raman spectra measured by immersing Ag25_HAp-800 in folic acid aqueous solutions at different concentrations ((a): $3 \times 10^{-6}$ mol/L, (b): $1.5 \times 10^{-6}$ mol/L, (c): $1.0 \times 10^{-6}$ mol/L, (d): $5.0 \times 10^{-6}$ mol/L, (e): $2.5 \times 10^{-6}$ mol/L, (f): $1.25 \times 10^{-6}$ mol/L).
Figure 35:
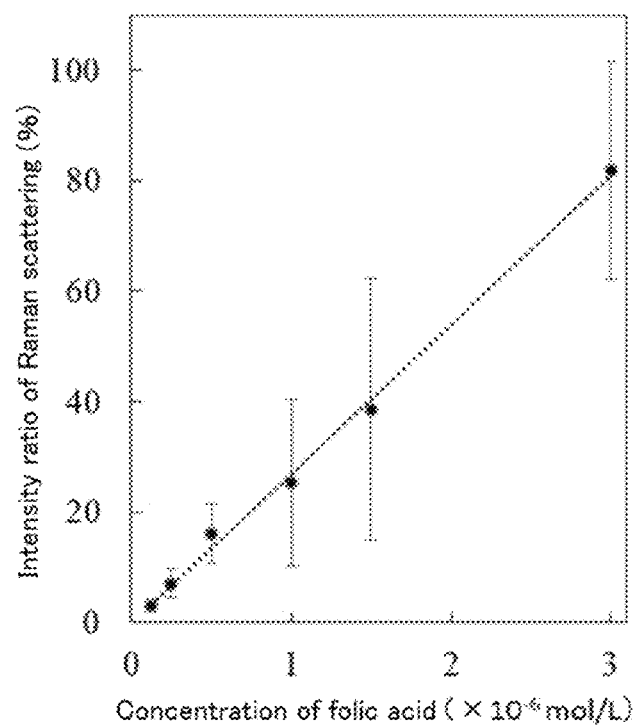
FIG. 35 is a graph obtained by plotting the intensity ratio of the Raman line of 966 cm$^{-1}$ attributable to the phosphate group of hydroxyapatite and the Raman line of 1589 cm$^{-1}$ attributable to C=C of folic acid with respect to folic acid concentration, in the measured Raman spectrum.

The silver-containing hydroxyapatite particles (Ag25_HAp-800) were added to sodium chloride aqueous solutions (0.06 mol/L) wherein folic acid concentrations were adjusted to $3 \times 10^{-6}$ mol/L, $1.5 \times 10^{-6}$ mol/L, $1.0 \times 10^{-6}$ mol/L, $0.5 \times 10^{-6}$ mol/L, $0.25 \times 10^{-6}$ mol/L, or $0.125 \times 10^{-6}$ mol/L, and Raman spectroscopic analysis was performed with a laser light source with a wavelength of 532.18 nm. Analysis was performed in the 100 μ$m^2$ to measure 4 points for each particle. The representative Raman spectra in each of samples measured at 2000 $cm^{-1}$ to 400 $cm^{-1}$ are shown in FIG. 34. The intensity ratio between the Raman line of 966 $cm^{-1}$ and the Raman line of 1589 $cm^{-1}$ attributed to C=C of folic acid was calculated at each measurement point, and an average was calculated. In this case, the intensity was calculated assuming that the background was approximated by the linear function. A graph in which the concentration of folic acid is plotted on the X-axis and the intensity ratio is plotted on the Y-axis, is shown in FIG. 35. As a result of linear approximation, a linear function of Y=26.96 X was obtained and the value of $R^2$ was 0.997. From these results, it was obvious that the concentration of folic acid correlates with the intensity ratio up to an extremely low concentration of $1.25 \times 10^{-7}$ mol/L.

INDUSTRIAL APPLICABILITY

The silver-containing calcium phosphate sintered body of the present invention may be used in various fields such as medical applications, living goods, photocatalysts, and air conditioning materials, as the antibacterial materials having antibacterial activity. Specifically, it is useful as an antimicrobial material in the medical field and can be used to prevent infections around implants such as peri-implantitis for a long time by using the same as an indwelling implant material. Further, the silver-containing calcium compound porous particle of the present invention can be used as a carrier for a test substance in Raman spectroscopic analysis.

Although the present invention has been described with reference to specific embodiments, various changes and modifications obvious to those skilled in the art are possible without departing from the scope of the appended claims.

The invention claimed is:

1. A silver-containing calcium phosphate sintered particle having silver particles therein, Therein an average particle diameter of the silver particles is 0.01 to 0.5 µm, and an average particle diameter of the silver-containing calcium phosphate sintered particle is 1.0 to 300 µm.

2. The silver-containing calcium phosphate sintered particle according to claim 1, wherein the silver particles are present at a grain boundary of the calcium phosphate sintered body.

3. The silver-containing calcium phosphate sintered particle according to claim 1, wherein 95% or more of the silver particles are contained within a radius of 80% from the center in a cross-section of the silver-containing calcium phosphate sintered particle.

4. The silver-containing calcium phosphate sintered particle according to claim 1, wherein an amount of the silver particles is 0.03 to 40% by weight.

5. The silver-containing calcium phosphate sintered particle according to claim 1, wherein five or more the silver particles are contained per a cross-section of 100 $\mu m^2$ of the silver-containing calcium phosphate sintered particle.

6. The silver-containing calcium phosphate sintered particle according to claim 1, wherein calcium phosphate is selected from the group consisting of hydroxyapatite, calcium dihydrogen phosphate, calcium dihydrogen phosphate hydrate, calcium monohydrogen phosphate, calcium monohydrogen phosphate hydrate, octacalcium phosphate, and tricalcium phosphate.

7. The silver-containing calcium phosphate sintered particle according to claim 1, wherein the silver-containing calcium phosphate sintered particle has an antibacterial property.

8. A method for preparing a silver-containing calcium phosphate sintered body, comprising steps of;

(1) applying a reducing agent to calcium phosphate porous particles, (2) immersing the reducing agent-applied calcium phosphate porous particle in an aqueous solution containing silver complex to precipitate silver particles within the calcium phosphate porous particles, and (3) calcining the silver particle-precipitated calcium phosphate porous p article.

9. The method for preparing a silver-containing calcium phosphate sintered body according to claim 8, wherein the reducing agent is aldehyde.

10. The method for preparing a silver-containing calcium phosphate sintered body according to claim 8, wherein the application of the reducing agent is an aldehyde vapor deposition.

11. The method for preparing a silver-containing calcium phosphate sintered body according to claim 8, wherein the aqueous solution containing silver complex is an ammoniacal silver nitrate aqueous solution.

12. The method for preparing a silver-containing calcium phosphate sintered body according to claim 8, wherein the silver particle-precipitated calcium phosphate porous particles are molded and the resulting molded body is calcined in the calcining step (3).

13. The method for preparing a silver-containing calcium phosphate sintered body according to claim 8, wherein the silver particle-precipitated calcium phosphate porous particles are calcined while pressure molding in the calcining step (3).

14. The method for preparing a silver-containing calcium phosphate sintered body according to claim 13, wherein the method of calcining and pressure molding is a hot pressing method or a spark plasma sintering method.

15. The method for preparing a silver-containing calcium phosphate sintered body according to claim 8, wherein calcium phosphate is selected from the group consisting of hydroxyapatite, calcium dihydrogen phosphate, calcium dihydrogen phosphate hydrate, calcium monohydrogen phosphate, calcium monohydrogen phosphate hydrate, octacalcium phosphate, and tricalcium phosphate.

16. An implant body comprising the silver-containing calcium phosphate sintered particle according to claim 1.

17. A silver-containing calcium compound porous particle containing silver particles, wherein an average particle diameter of the silver particle is 0.01 to 0.5 µm, and an average particle diameter of the silver-containing calcium compound porous particle is 1.0 to 300 µm.

18. The silver-containing calcium compound porous particle according to claim 17, wherein an amount of the silver particles is 0.03 to 40% by weight.

19. The silver-containing calcium compound porous particle according to claim 17, wherein the calcium compound is selected from the group consisting of calcium phosphate, calcium carbonate, calcium sulfate, and calcium oxide.

20. The silver-containing calcium compound porous particle according to claim 19, wherein calcium phosphate is selected from the group consisting of hydroxyapatite, calcium dihydrogen phosphate, calcium dihydrogen phosphate hydrate, calcium monohydrogen phosphate, calcium monohydrogen phosphate hydrate, octacalcium phosphate, and tricalcium phosphate.

21. A method for preparing a silver-containing calcium compound porous particle, comprising steps of:

(1) applying a reducing agent to the calcium compound porous particle, and (2) immersing the reducing agent-applied calcium compound porous particle in an aqueous solution containing silver complex to precipitate silver particles on a surface of particle constituting the calcium compound porous particle.

22. The method for preparing a silver-containing calcium compound porous particle according to claim 21, wherein the reducing agent is aldehyde.

23. The method for preparing a silver-containing calcium compound porous particle according to claim 21, wherein the application of the reducing agent is an aldehyde vapor deposition.

24. The method for preparing a silver-containing calcium compound porous particle according to claim 21, wherein the aqueous solution containing silver complex is an ammoniacal silver nitrate aqueous solution.

25. A method of Raman spectroscopic analysis, comprising the steps of:
   (1) applying a substance to be tested to the silver-containing calcium compound porous particle according to claim 17,
   (2) irradiating the substance-applied, silver-containing calcium compound porous particle with laser light, and
   (3) detecting a Raman scattering light.

26. The method of Raman spectroscopic analysis according to claim 25, wherein the application in the step (1) is done by immersion of the silver-containing calcium compound porous particles into a liquid containing the substance to be tested, or a placement of the liquid containing the substance to be tested on the silver-containing calcium compound porous particles.

\* \* \* \* \*